(12) United States Patent
Terunuma et al.

(10) Patent No.: US 8,741,561 B2
(45) Date of Patent: Jun. 3, 2014

(54) GENE SETS FOR DETECTION OF ULTRAVIOLET A EXPOSURE AND METHODS OF USE THEREOF

(75) Inventors: Atsushi Terunuma, Rockville, MD (US); Jonathan Vogel, Bethesda, MD (US); Elizabeth Falloon, legal representative, Bethesda, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 13/580,832

(22) PCT Filed: Feb. 24, 2011

(86) PCT No.: PCT/US2011/026086
§ 371 (c)(1),
(2), (4) Date: Aug. 23, 2012

(87) PCT Pub. No.: WO2011/109224
PCT Pub. Date: Sep. 9, 2011

(65) Prior Publication Data
US 2013/0065781 A1    Mar. 14, 2013

Related U.S. Application Data

(60) Provisional application No. 61/309,179, filed on Mar. 1, 2010.

(51) Int. Cl.
*C12Q 1/68*    (2006.01)

(52) U.S. Cl.
USPC .......................................................... 435/6.1

(58) Field of Classification Search
None
See application file for complete search history.

(56) References Cited

U.S. PATENT DOCUMENTS

| | | |
|---|---|---|
| 7,363,165 B2 | 4/2008 | Tusher et al. |
| 2002/0197633 A1 | 12/2002 | Jones et al. |
| 2004/0152109 A1 | 8/2004 | Chu et al. |
| 2004/0185485 A1 | 9/2004 | Blumenberg |
| 2007/0031356 A1 | 2/2007 | Buchwald Hunziker et al. |
| 2007/0148106 A1 | 6/2007 | Wertz et al. |

FOREIGN PATENT DOCUMENTS

| | | |
|---|---|---|
| FR | 2 879 747 | 6/2006 |
| WO | WO 02/20849 | 3/2002 |
| WO | WO 02/090934 | 11/2002 |

OTHER PUBLICATIONS

Gruber et al., FASEB Journal, 2009, vol. 24, pp. 1-10.*
Reiner et al., Bioinformatics, 2003, vol. 19, pp. 368-375.*
Abe et al., "Rapid and Preferential Induction of ATF3 Transcription in Response to Low Doses of UVA Light," *Biochem. Biophys. Res. Comm.*, vol. 310:1168-1174, 2003.
Becker et al. "Detection of Differentially Regulated Genes in Keratinocytes by cDNA Array Hybridization: Hsp27 and Other Novel Players in Response to Artificial Ultraviolet Radiation," *J. Invest. Dermatol.*, vol. 116:983-988, 2001.
de la Fuente et al., "Identification of Genes Responsive to Solar Simulated UV Radiation in Human Monocyte-Derived Dendritic Cells," *PLoS ONE*, vol. 4(8):e6735, 2009.
Efron and Tibshirani, "On Testing the Significance of Sets of Genes," *Ann. Appl. Stat.* 1(1):107-129, 2007.
Enk et al., "Gene Expression Profiling of in vivo UVB-Irradiated Human Epidermis," *Photodermatol. Photoimmunol. Photomed.*, vol. 20:129-137, 2004.
Gruber et al., "NF-E2-Related Factor 2 Regulates the Stress Response to UVA-1-Oxidized Phospholipids in Skin Cells," *FASEB J.*, vol. 24:39-48, 2010.
Hazane et al., "Ageing Effects on the Expression of Cell Defence Genes After UVA Irradiation in Human Male Cutaneous Fibroblasts Using cDNA Arrays," *J. Photochem. Photobiol.*, vol. 79:171-190, 2005.
He et al., "Expression Profiling of Human Keratinocyte Response to Ultraviolet A: Implications in Apoptosis," *J. Invest. Dermatol.*, vol. 122:533-543, 2004.
Jean et al., "The Expression of Genes Induced in Melanocytes by Exposure to 365-nm UVA: Study by cDNA Arrays and Real-Time Quantitative RT-PCR," *Biochim. Biophys. Acta*, vol. 1522:89-96, 2001.
Koch-Paiz et al., "Functional Genomics of UV Radiation Responses in Human Cells," *Mutat. Res.*, vol. 549:65-78, 2004.
Stapelberg et al., "The Alternative Complement Pathway Seems to be a UVA Sensor that Leads to Systemic Immunosuppression," *J. Invest. Dermatol.*, vol. 129:2694-2701, 2009.
Subramanian et al., "GSEA-P: A Desktop Application for Gene Set Enrichment Analysis," *Bioinformatics*, vol. 23(23):3251-3253, 2007.
Subramanian et al., "Gene Set Enrichment Analysis: A Knowledge-Based Approach for Interpreting Genome-Wide Expression Profiles," *Proc. Natl. Acad. Sci. USA*, vol. 102(43):15545-15550, 2005.
Yang et al., "Expression Profiling of UVB Response in Melanocytes Identifies a Set of p. 53-Target Genes," *J. Invest. Dermatol.*, vol. 126:2490-2506, 2006.

* cited by examiner

*Primary Examiner* — Anne Gussow
*Assistant Examiner* — Mindy G Brown
(74) *Attorney, Agent, or Firm* — Klarquist Sparkman, LLP

(57) ABSTRACT

Ultraviolet radiation (UVR) has profound effects on human skin. However, its effects on the global transcriptome in vivo have not been well characterized. In addition, the contribution of the UVA component of UVR has not been previously assessed in vivo. Disclosed herein is the identification of sets of genes that are either up-regulated or down-regulated in response to UVA exposure. The gene sets described herein can be used to accurately identify skin samples that have been exposed to UVA and to assess the ability of a sun protection product to block the effects of UVA.

28 Claims, 11 Drawing Sheets

(FDR <1%; |log(fold-change)| >0.5)

(FDR <30%)

(FDR =0%)

ssUVR

(FDR <1%; |log(fold change)| >0.5)

ssUVA

(FDR <1%; |log(fold change)| >0.5)

FIG. 5

Representative gene sets that were affected by 1 MED ssUVR

| | | ssUVR | | UVA | | sunscreen + ssUVR | |
|---|---|---|---|---|---|---|---|
| | | Score | FDR | Score | FDR | Score | FDR |
| P53 and nucleotide metabolism | HSA00240_PYRIMIDINE_METABOLISM | 0.36 | 0% | 0.23 | 86% | 0.14 | 93% |
| | HSA00230_PURINE_METABOLISM | 0.32 | 0% | 0.03 | 94% | 0.14 | 57% |
| | NUCLEOTIDE_METABOLISM | 1.06 | 22% | 0.27 | 87% | 0.59 | 84% |
| | PYRIMIDINE_METABOLISM | 0.68 | 22% | 0.19 | 87% | 0.13 | 94% |
| | PURINE_METABOLISM | 0.53 | 22% | 0.09 | 79% | 0.22 | 0% |
| | P53PATHWAY | 0.72 | 28% | 0.04 | 94% | -0.12 | 93% |
| | P53GENES_ALL | 0.83 | 29% | -0.48 | 74% | 0.13 | 93% |
| Proteasome | PROTEASOMEPATHWAY | 2.36 | 0% | 0.79 | 68% | 0.80 | 78% |
| | PROTEASOME | 2.27 | 0% | 0.62 | 60% | 0.81 | 83% |
| | HSA03050_PROTEASOME | 2.24 | 0% | 0.84 | 56% | 1.02 | 38% |
| | PROTEASOME_DEGRADATI | 1.42 | 0% | 0.37 | 80% | 0.50 | 85% |
| MYC | SCHUMACHER_MYC_UP | 1.66 | 0% | 0.91 | 35% | 0.52 | 85% |
| | COLLER_MYC_UP | 1.45 | 24% | 1.37 | 14% | 0.49 | 86% |
| | MYC_TARGETS | 1.05 | 0% | 0.69 | 58% | 0.35 | 85% |
| | MENSSEN_MYC_UP | 1.32 | 29% | 0.49 | 82% | 0.23 | 95% |
| RAS | CROONQUIST_RAS_STROMA_DN | -1.72 | 0% | -1.37 | 49% | -1.25 | 0% |
| VEGF | VEGF_MMMEC_ALL_UP | -0.35 | 0% | -0.09 | 88% | -0.06 | 92% |
| TGF-β | TGFBETA_C1_UP | -0.56 | 67% | -0.13 | 92% | -0.95 | 0% |
| | TGFBETA_C2_UP | -0.66 | 83% | -0.42 | 90% | -0.91 | 0% |
| | TGFBETA_EARLY_UP | -0.51 | 75% | -0.18 | 93% | -0.80 | 0% |
| | TGFBETA_ALL_UP | -0.38 | 80% | -0.21 | 84% | -0.46 | 0% |

Score: enrichment scores calculated by GSA software (Stanford University)
FDR: false discovery rate calculated by GSA

FIG. 6

Gene set analysis with custom gene sets on various skin conditions

|  | UP_by_A | | DOWN_by_A | | UP_in_SS | | DOWN_in_SS | |
|---|---|---|---|---|---|---|---|---|
|  | Score | FDR | Score | FDR | Score | FDR | Score | FDR |
| psoriasis | -0.19 | 86% | 1.23 | 84% | 0.61 | 87% | 0.81 | 87% |
| atopic dermatitis | 0.28 | 75% | -0.66 | 85% | -0.40 | 87% | -0.98 | 85% |
| squamous cell carcinoma | -0.10 | 100% | -0.79 | 78% | -0.15 | 100% | -0.28 | 100% |
| actinic keratosis | -0.39 | 87% | -0.53 | 64% | -0.91 | 63% | 0.41 | 78% |
| malignant melanoma | -0.51 | 78% | -0.21 | 94% | -1.21 | 0% | -0.40 | 86% |
| nevus | -1.22 | 82% | -0.38 | 94% | -0.26 | 98% | 0.12 | 92% |
| sunscreen + UVR, 1 MED | 2.67 | 0% | -2.15 | 0% | n.a. | n.a. | n.a. | n.a. |
| sunscreen + UVR, 100 J/m² | 1.86 | 0% | -1.22 | 0% | n.a. | n.a. | n.a. | n.a. |
| sunscreen + UVR, 0.1 MED | 1.04 | 0% | -1.41 | 0% | n.a. | n.a. | n.a. | n.a. |
| UVA, 1 MED | n.a. | n.a. | n.a. | n.a. | 4.40 | 0% | -1.39 | 0% |
| UVA, 100 J/m² | n.a. | n.a. | n.a. | n.a. | 3.28 | 0% | -1.45 | 0% |
| UVA, 0.1 MED | n.a. | n.a. | n.a. | n.a. | 1.73 | 56% | -0.37 | 92% |

Score: enrichment scores calculated by GSA software (Stanford University)
FDA: false discover rate calculated by GSA

FIG. 7

Genes that were differentially expressed in 1 MED UVA, but not UVR, at FDR =)%

| Affy ID | Gene Symbol | Name of Gene Product | UVA, 1 MED | | UVR, 1 MED | | SS + UVR, 1 MED | |
|---|---|---|---|---|---|---|---|---|
| | | | Fold Change | FDR | Fold Change | FDR | Fold Change | FDR |
| 206465_at | ACSBG1 | Acyl-CoA synthetase bubblegum family member 1 | 2.52 | 0.00% | 2.25 | 4.34% | 1.01 | 73.85% |
| 205623_at | ALDH3A1 | Aldehyde dehydrogenase 3 family, member A1 | 2.05 | 0.00% | 1.13 | 61.34% | 1.46 | 23.19% |
| 220026_at | CLCA4 | Calcium-activated chloride channel regulator 4 | 1.57 | 0.00% | 1.34 | 14.38% | 1.84 | 0.00% |
| 205019_s_at | VIPR1 | Vasoactive intestinal polypeptide receptor 1 | 1.44 | 0.00% | 0.95 | 39.79% | 1.22 | 75.19% |

Five genes that were differentially expressed in sunscreen + 1 MED UVR at FDR =0%

| Affy ID | Gene Symbol | Name of Gene Product | SS + UVR | | UVR | | UVA | |
|---|---|---|---|---|---|---|---|---|
| | | | Fold Change | FDR | Fold Change | FDR | Fold Change | FDR |
| 209507_at | RPA3* | Replication protein A 14 kDa subunit | 1.61 | 0.00% | 1.72 | 0.00% | 1.50 | 0.00% |
| 216594_x_at | AKR1C1* | Aldo-keto reductase family 1 member C1 | 1.59 | 0.00% | 1.60 | 0.00% | 1.55 | 0.00% |
| 206630_at | TYR** | Tyrosinase | 1.52 | 0.00% | 1.60 | 0.00% | 1.66 | 4.97% |
| 201660_at | ACSL3 | Long-chain acyl-CoA synthetase 3 | 1.55 | 0.00% | 1.35 | 0.26% | 1.14 | 88.58% |
| 220026_at | CLCA4 | Calcium-activated chloride channel regulator 4 | 1.84 | 0.00% | 1.34 | 14.38% | 1.57 | 0.00% |

Seven genes that were affected either by 1 MED UVR or UVA, but not by sunscreen + UVR

| Affy ID | Gene Symbol | Name of Gene Product | UVA | | UVR | | SS + UVR | |
|---|---|---|---|---|---|---|---|---|
| | | | Fold Change | FDR | Fold Change | FDR | Fold Change | FDR |
| 203574_at | NFIL3 | Nuclear factor interleukin-3-regulated protein | 2.42 | 0.00% | 2.92 | 0.00% | 1.85 | 10.37% |
| 215322_at | n.a. | DKFZp434A202 | 2.04 | 0.00% | 1.52 | 0.35% | 2.30 | 7.18% |
| 209122_at | PLIN2 | Perilipin-2 | 1.99 | 0.00% | 1.53 | 0.26% | 1.56 | 57.43% |
| 220178_at | C19orf28 | Uncharacterized MFS-type transporter C19orf28 | 1.80 | 0.00% | 1.90 | 0.00% | 1.62 | 52.51% |
| 204151_x_at | AKR1C1 | Aldo-keto reductase family 1 member C1 | 1.55 | 0.00% | 1.61 | 0.00% | 1.41 | 7.18% |
| 209699_x_at | AKR1C2 | Aldo-keto reductase family 1 member C2 | 1.54 | 0.00% | 1.69 | 0.00% | 1.51 | 9.72% |
| 203119_at | CCDC86 | Coiled-coil domain-containing protein 86 | 1.51 | 0.00% | 1.92 | 0.00% | 1.44 | 42.53% |

FIG. 10

Ingenuity canonical pathways that were associated with genes up-regulated by 1 MED UVR

| Ingenuity Canonical Pathways | P value | Molecules |
|---|---|---|
| Polyamine Regulation in Colon Cancer | 0.000 | PSMB3, PSMA3, PSMB10, PSMA7, PSMB6, ODC1, PSMC5, PSMC6, PSMD14, PSMA2, PSMC2, PSMB4, PSMA6, PSMB5, PSMD13, PSMC4, PSMD6, PSMD3, PSMA1, PSMD8, PSMD11, PSMB7, PSMC1, PSMB2, PSMD2, PSMA5, PSMD12, PSMA4, PSMB1, PSMD1, PSMD4 |
| Mitochondrial Dysfunction | 0.000 | HSD17B10, SDHB, COX7B, NDUFA9, PSENEN, NDUFB8, NDUFA2, PDHA1, NDUFS1, PARK7, NDUFAB1, NDUFS6, NDUFB6, UQCRFS1, AIFM1, NDUFA8, NDUFV1, COX17, NDUFB3, COX7A2, NDUFS7, GLRX2, NDUFS3, NDUFA13, ATP5C1, NDUFS5, NDUFS8, NDUFV2, ATP5B, NDUFA6, UQCRC2, COX5A, CYC5, CYC1, UQCRC1, NDUFB2 |
| Protein Ubiquitination Pathway | 0.000 | PSMB3, USP14, PSMA3, UBE2A, PSMB10, PSMA7, PSMB6, PSMC5, USP3, PSMC6, PSMD14, PSMC2, PSMA2, PSMB4, UCHL3, PSMA6, PSMB5, USP15, PSMD13, PSME2, PSMC4, PSMD6, PSMD3, UBE2S, PSMA1, PSMD8, UBE2G2, HSPA8, PSMB7, PSMD11, PSME1, PSMC1, PSMB2, PSMD2, PSMA5, PSMD12, PSMB1, PSMA4, ANAPC5, HSP90AA1, PSMD1, UBA1, PSMD4, UBE2C |
| RAN Signaling | 0.000 | CSE1L, KPNA2, TNPO1, RAN, RANBP1, RCC1, IPO5, RANGAP1 |
| Nucleotide Excision Repair Pathway | 0.009 | POLR2G, POLR2F, POLR2L, RPA3, ERCC1, CDK7, POLR2H, RAD23B |
| Cleavage and Polyadenylation of Pre-mRNA | 0.052 | PAPOLA, CSTF3, CPSF4 |
| Role of CHK Proteins in Cell Cycle Checkpoint Control | 0.068 | TP53, E2F6, PCNA, CDKN1A, CDC2, NBN |
| p53 Signaling | 0.078 | CCNG1, SCO2, TP53, PCNA, GADD45A, CDK4, CDKN1A, TNFRSF10B, C12ORF5, BAX, DRAM1, TP53I3 |
| Cell Cycle: G2/M DNA Damage Checkpoint Regulation | 0.095 | TP53, GADD45A, YWHAB, CDK7, CDKN1A, CDC2 |

FIG. 11 Gene sets that were affected by UVR, and not blocked by sunscreen at FDR <30%

| Gene_set_name | Description | UVR + sunscreen | | UVR | |
|---|---|---|---|---|---|
| | | Score | FDR | Score | FDR |
| XU_ATRA_PLUSNSC_DN | Down-regulated by all-trans retinoic acid | 1.91 | 0% | 2.00 | 24% |
| WANG_MLL_CBP_VS_GMP_UP | Up-regulated by MLL-CBP expression | 0.54 | 0% | 0.99 | 0% |
| N_GLYCAN_BIOSYNTHESIS | Associated with N-glycan biosynthesis | 0.47 | 0% | 0.66 | 14% |
| HSC_INTERMEDIATEPROGENITORS_SHARED | Up-regulated in mouse hematopoietic intermediate progenitors from adult bone marrow and fetal liver | 0.40 | 0% | 0.43 | 24% |
| ZHAN_MULTIPLE_MYELOMA_SUBCL ASSES_DIFF | Differentially expressed between multiple myeloma subgroups | 0.38 | 28% | 0.97 | 14% |
| HSC_INTERMEDIATEPROGENITORS_ADULT | Up-regulated in mouse hematopoietic intermediate progenitors from adult bone marrow | 0.35 | 0% | 0.41 | 0% |
| HSC_INTERMEDIATEPROGENITORS_FETAL | Up-regulated in mouse hematopoietic intermediate progenitors from fetal liver | 0.34 | 0% | 0.41 | 29% |
| TESTIS_EXPRESSED_GENES | Related to testis | 0.29 | 0% | 0.27 | 24% |
| PGC | Associated with PGC | 0.29 | 0% | 0.60 | 0% |
| PURINE_METABOLISM | Associated with purine metabolism | 0.22 | 0% | 0.53 | 22% |
| HOFFMANN_BIVSBII_BI | Differentially expressed between Pre-BI and Large Pre-BII cells | 0.19 | 0% | 0.16 | 29% |
| SHEPARD_CRASH_AND_BURN_MUT VS_WT_UP | Up-regulated in the crash & burn zebra fish mutant | 0.15 | 0% | 0.51 | 24% |
| CROONQUIST_RAS_STROMA_DN | Downregulated in multiple myeloma cells with N-ras-activating mutations vs. those co-cultured with bone marrow stromal cells. | -1.26 | 0% | -1.72 | 0% |
| IRS_KO_ADIP_DN | Progressively down-regulated in brown preadipocytes from 4 Irs-knockout mouse lines with increasingly severe defects in adipocyte differentiation | -0.59 | 0% | -0.77 | 0% |
| MYOD_NIH3T3_DN | Down-regulated at 24 hours in NIH 3T3 murine fibroblasts following transduction with MyoD and incubation in differentiation medium | -0.39 | 0% | -0.56 | 0% |

FIG. 12

| | | | | | | | | | |
|---|---|---|---|---|---|---|---|---|---|
| UP_by_A | ACSBG1 | ADFP | ADH5 | AKR1C1 | AKR1C2 | ALDH3A1 | AOF2 | BDH2 | BRD1 | C19orf28 |
| | C20orf24 | CAPN3 | CCDC86 | CDC34 | CLCA4 | CLTB | CTSC | DDX19A | DDX5 | ELAC2 |
| | FGFBP1 | FLJ14154 | HK2 | HMG20B | HOXB7 | KLK10 | LONRF1 | MAP2K3 | MYC | NFIL3 |
| | OCA2 | P11 | PMVK | PQBP1 | PRKCSH | RPA3 | RPL10 | SLC25A4 | SLTM | SPRR1A |
| | STX4 | TMEM160 | TPD52L2 | TRIM22 | TSFM | TUBGCP2 | TYR | VIPR1 | WNK1 | |
| DOWN_by_A | CAV1 | CCNG2 | CD1A | CD207 | CLDND1 | FAS | FER1L3 | GOLPH3L | H3F3B | HSPA2 |
| | IL33 | KIAA0515 | KIT | KRT31 | LAMB4 | MCCC2 | PPP1R3C | SCUBE2 | SP110 | THBS2 |
| | TMEM43 | ZNF652 | ZSCAN18 | | | | | | | |
| UP_in_SS | ACSL3 | AKR1C1 | AKR1C2 | CLCA4 | CSE1L | IDH3B | LONRF1 | MAP2K3 | MXRA5 | MYD88 |
| | NHP2L1 | NPM1 | PER3 | PSMA1 | RPA3 | TYR | | | | |
| DOWN_in_SS | ADD3 | APP | APPBP2 | AQP1 | BTG1 | C1orf63 | C3orf14 | C9orf95 | CAV1 | CCNG2 |
| | CDC42EP4 | CDH13 | COL1A1 | COL1A2 | COL4A2 | COL4A6 | DKK3 | FASTKD3 | GOLPH3L | GPD1L |
| | HPGD | HSPA2 | ID2 | ID4 | IFRD1 | IGFBP5 | ITGB3BP | LIAS | MRFAP1L1 | NR1D1 |
| | OPTN | PCMTD2 | PPAP2B | PPFIBP1 | PPP1CB | RALGDS | SPARC | TGFBI | THUMPD1 | TPM1 |
| | TXNIP | ZNF274 | | | | | | | | |

GENE SETS FOR DETECTION OF ULTRAVIOLET A EXPOSURE AND METHODS OF USE THEREOF

CROSS REFERENCE TO RELATED APPLICATIONS

This application is the U.S. National Stage of International Application No. PCT/US2011/026086, filed Feb. 24, 2011, published in English under PCT Article 21(2), which claims the benefit of U.S. Provisional Application No. 61/309,179, filed Mar. 1, 2010, which is herein incorporated by reference in its entirety.

FIELD

This disclosure concerns effects of ultraviolet A (UVA) on skin. In particular, this disclosure relates to the identification of gene sets (e.g., human gene sets) for detecting exposure to UVA and their use in evaluating the efficacy of sun protection products against the effects of UVA on animal (e.g., human) skin.

BACKGROUND

Ultraviolet irradiation causes skin photoaging and cancer (Yaar & Gilchrest, Br J Dermatol 157:874-887, 2007; Kulms & Schwarz, J Investig Dermatol Symp Proc 7:46-50, 2002; Matsumura & Ananthaswamy, Toxicol Appl Pharmacol 195:298-308, 2004; Gilchrest et al., N Engl J Med 340: 1341-1348, 1999; Miller et al., Photochem Photobiol 68:63-70, 1998; Fisher et al., N. Engl J Med 337:1419-1428, 1997; Kraemer, Proc Natl Acad Sci USA 94:11-14, 1997; Gilchrest, "Photodamage," New York: Blackwell Scientific, 1995). Solar ultraviolet C (UVC) and much of ultraviolet B (UVB) are blocked by the ozone layer and oxygen in the earth's atmosphere. Approximately 95% of the ultraviolet radiation that reaches the earth's surface is ultraviolet A (UVA) while the remainder is UVB (Miller et al., Photochem Photobiol 68:63-70, 1998; Solar and ultraviolet radiation: World Health Organization, 1997), which plays a critical role in carcinogenesis by (1) forming DNA cyclobutane pyrimidine dimers (CPDs) and pyrimidine (6-4) pyrimidone photoproducts (Gilchrest et al., N Engl JMed 340:1341-8, 1999; Zhao et al., Int J Cancer 98:331-4, 2002), and (2) inducing immunosuppression (Noonan et al., Pigment Cell Res 16:16-25, 2003). Because of its longer wave length, UVA can pass through window glass and clothing, and penetrate deeper into the skin (Wang et al., J Am Acad Dermatol 44:837-846, 2001).

UVA radiation has been thought to be relatively innocuous because the amount of UVA absorbed by DNA is several orders of magnitude lower than that of UVB, but it has become evident that UVA damages DNA indirectly through generating oxidative free radicals and directly by inducing the formation of CPDs like UVB (Mouret et al., Proc Natl Acad Sci USA 103:13765-13770, 2006). Additionally, UVA has been suggested to play a role in melanoma development (Gasparro, Environ Health Perspect 108 Suppl 1:71-78, 2000; Setlow, J Investig Dermatol Symp Proc 4:46-49, 1999; Garland et al., Ann Epidemiol 3:103-110, 1993). Immune suppression may also be induced by UVA, further enhancing susceptibility to cutaneous malignancy (Nghiem et al., J Invest Dermatol 117:1193-1199, 2001; Bestak & Halliday, Photochem Photobiol 64:969-974, 1996).

Growing public awareness of the damaging effects of ultraviolet light/radiation in the 1960s led to the emergence of sun safety campaigns and the development of various sunscreens. The FDA now requires that all over-the-counter sunscreens undergo sun protection factor (SPF) testing. SPF is defined as a fold-increase of ultraviolet light exposure time needed to cause sunburn. For example, SPF 15 sunscreens extend the exposure time to induce erythema by 15-fold. Because UVB is 1,000 times more effective than UVA in producing erythema, SPF is a better measure of UVB blockade than UVA blockade. Currently, there are no standard in vivo assays to evaluate the UVA effects on human (or any other animal) skin, and it is difficult to assess a sunscreen for its real UVA protection efficacy despite the fact that many sunscreens on the market are advertised as blocking UVA in addition to UVB (Gasparro, Environ Health Perspect 108 Suppl 1:71-78, 2000; Lowe, Dermatol Clin 24:9-17, 2006; Rosenstein et al., Photodermatol Photoimmunol Photomed 15:75-80, 1999).

Although effects of ultraviolet light on the transcriptome of cultured keratinocytes have been reported (Becker et al., J Invest Dermatol 116:983-988, 2001; Dazard et al., Oncogene 22:2993-3006, 2003; Lee et al., Br J Dermatol 152:52-59, 2005; Li et al., FASEB J 15:2533-2535, 2001; Murakami et al., J Dermatol Sci 27:121-129, 2001; Pisarchik et al., Gene 341:199-207, 2004; Sesto et al., Proc Natl Acad Sci USA 99:2965-2970, 2002; Takao et al., Photodermatol Photoimmunol Photomed 18:5-13, 2002; Adachi et al., DNA Cell Biol 22:665-677, 2003), additional studies are needed to characterize how solar-simulated ultraviolet radiation (ssUVR) and UVA modify the global transcriptome of human skin in vivo (Enk et al., Photodermatol Photoimmunol Photomed 20:129-137, 2004; Blumenberg, OMICS 10:243-260, 2006).

SUMMARY

Accordingly, described herein are studies for evaluating the effects of ssUVR and UVA on human skin. The in vivo approach disclosed herein to assess the effects of ssUVR and UVA by gene set analysis of expression microarray data lends insight into the molecular events induced by ssUVR and UVA, provides methods to study and measure the extent that sunscreen blocks ssUVR effects, and reveals unexpected effects of sunscreen application.

Disclosed herein is the identification of sets of genes that are either up-regulated or down-regulated in response to UVA exposure. The gene sets described herein can be used to accurately identify skin samples that have been exposed to UVA and to assess the ability of a sun protection product to block the effects of UVA.

Provided herein is a method for detecting exposure of a skin sample to UVA by detecting expression of a plurality of genes in the skin sample. In some embodiments, the plurality of genes includes (i) AKR1C2, NFIL3, MAP2K3 and BRD1; (ii) CAV1, GOLPH3L, H3F3B and SP110; or both (i) a (ii). In alternative embodiments, the plurality of genes includes AKR1C2, NFIL3 and MAP2K3, or includes AKR1C2, NFIL3 and BRD1. The plurality of genes optionally further includes one or more additional genes from the custom gene sets UP_by_A and DOWN_by_A as described herein. In some embodiments, the method further includes analyzing the gene expression data by gene set analysis using the custom UVA gene sets disclosed herein.

Further provided is a method for determining the efficacy of a sun protection product for providing protection against the effects of UVA by treating the skin of a test subject with the sun protection product; exposing the skin of the test subject to UVA; and detecting expression of a plurality of genes in a skin sample from the subject. In some embodiments, the plurality of genes includes (i) AKR1C2, NFIL3, MAP2K3 and BRD1; (ii) CAV1, GOLPH3L, H3F3B and SP110; or both (i) a (ii). In alternative embodiments, the plurality of genes includes AKR1C2, NFIL3 and MAP2K3, or includes AKR1C2, NFIL3 and BRD1. The plurality of genes optionally further includes one or more additional genes from the custom gene sets UP_by_A and DOWN_by_A. In some embodiments, the method further includes analyzing the gene expression data by gene set analysis using the custom UVA gene sets disclosed herein.

Also provided herein is a method of calculating the maximum dose (termed A-max) of UVR at which a sun protection product blocks or inhibits the effects of the UVA component of UVR. In some embodiments, the method includes treating the skin of a test subject with the sun protection product; exposing the skin of the test subject to multiple different doses of UVA; obtaining a skin sample for each UVA dose from the subject; detecting expression of a plurality of genes associated with exposure to UVA; and analyzing the gene expression data using gene set analysis and the custom UVA gene sets disclosed herein.

The foregoing and other objects, features, and advantages of the invention will become more apparent from the following detailed description, which proceeds with reference to the accompanying figures.

BRIEF DESCRIPTION OF THE DRAWINGS

In the figures described below, the dose of ssUVR is expressed as minimal erythema dose (MED) or $J/m^2$. The dose of UVA is expressed as the dose of ssUVR (in MED or $J/m^2$) before applying a filter to remove UVB.

FIG. 5 is a table showing representative gene sets that were affected by 1 MED ssUVR.

FIG. 6 is a table showing the results of gene set analysis with custom gene sets on various skin conditions.

FIG. 7 is a table showing genes that were differentially expressed in 1 MED UVA, but not ssUVR.

FIG. 8 is a table listing five genes that were differentially expressed in sunscreen+1 MED ssUVR.

FIG. 9 is a table listing seven genes that were affected either by 1 MED UVR or UVA, but not by sunscreen plus ssUVR.

FIG. 10 is a table showing canonical pathways that were associated with genes up-regulated by 1 MED ssUVR.

FIG. 11 is a table listing gene sets that were affected by ssUVR, and not blocked by sunscreen at FDR<30%.

FIG. 12 is a table showing genes in the custom gene sets UP_by_A, DOWN_by_A, UP_in_SS and DOWN_in_SS.

DETAILED DESCRIPTION

I. Introduction

Figure 1A:
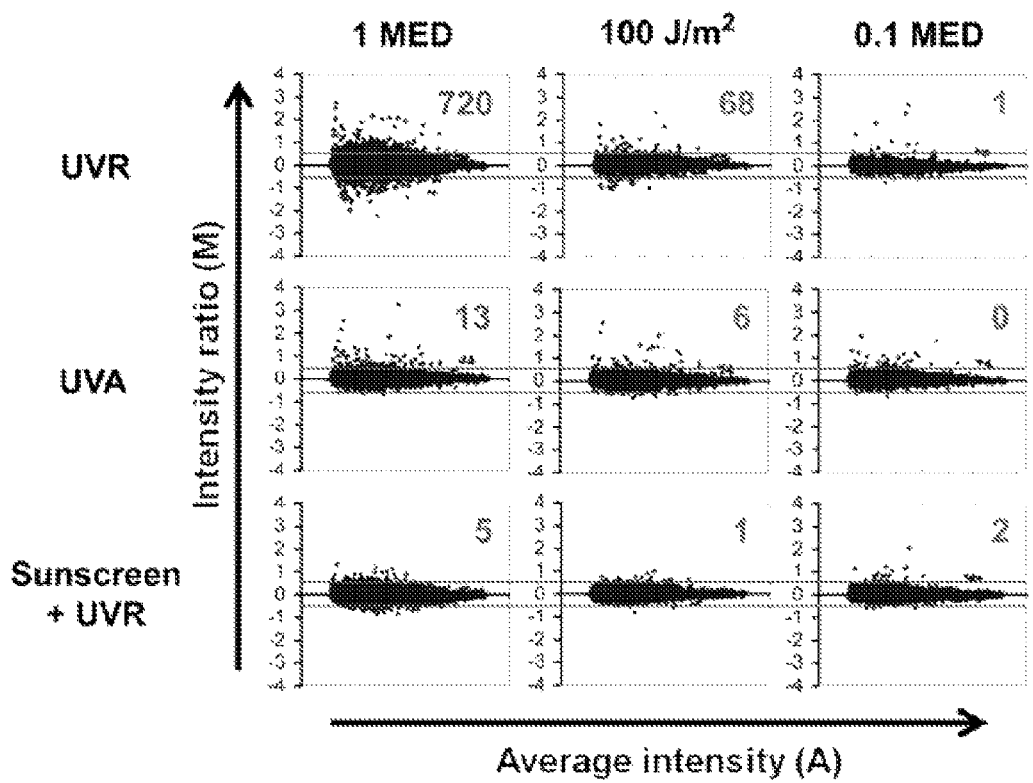
FIG. 1A is a set of microarray intensity ratio-average (M-A) plots showing the number of differentially expressed genes (false discovery rate (FDR)<1%; |log(fold-change)|>0.5) in skin treated with solar-simulated ultraviolet radiation (ssUVR) (n=16), ultraviolet A (UVA) (n=8), or sunscreen+ssUVR (n=6) at doses of 1 minimal erythema dose (MED), 100 $J/m^2$ and 0.1 MED, compared to non-exposed control skin. The horizontal lines at the center of the plots indicate the threshold for fold change. Due to the other criterion of FDR<1%, the numbers of dots above the threshold lines are more than the gene counts indicated in each M-A plot. X-axis: average intensity (A); Y-axis: the intensity ratio (M).

Solar radiation has profound effects on skin, including human skin. However, its effects on the global transcriptome in vivo have not been well characterized. Further, the contributions of the UVA component and the alterations in transcriptome responses induced by topical sunscreen have not been assessed in vivo.

For the studies disclosed herein, the skin of 20 donors was exposed to solar-simulated ultraviolet radiation (ssUVR), which includes ultraviolet B (UVB), UVA and visible light, at 1 minimal erythema dose (MED), 0.1 MED or 100 $J/m^2$, with or without pre-treatment with an FDA-standardized sunscreen, or the skin was exposed to the UVA component alone (by filtering out the UVB component of ssUVR). Skin sample biopsies were analyzed for changes in 14,500 genes of the human transcriptome using expression microarrays. Genes that were up- or down-regulated by UVA were utilized to create UVA gene sets that probe the transcriptome of various skin conditions for signatures of UVA exposure.

As disclosed herein, ssUVR-induced transcriptional changes indicate activation of oncogenic P53, MYC and RAS signaling pathways. Gene set analysis demonstrated that some important ssUVR effects, including RAS signal activation, were not completely blocked by an FDA-standardized sunscreen. Furthermore, the UVA gene sets detected unambiguous UVA transcriptional signatures (that is, consistent changes in expression of sets of genes) in skin that had been pretreated with sunscreen prior to ssUVR exposure at sub-erythemogenic doses.

Gene set analysis with custom UVA gene sets provides an extremely sensitive and quantitative indicator of UVA exposure, and offers a unique strategy to assess the efficacy of sun protection products in protecting skin against the adverse biological effects of UVA.

II. Abbreviations

| | |
|---|---|
| CPD | cyclobutane pyrimidine dimers |
| FDR | false discovery rate |
| GSA | gene set analysis |
| MED | minimal erythema dose |
| PCR | polymerase chain reaction |
| RT-PCR | reverse transcriptase PCR |
| SAM | significance analysis of microarrays |
| SPF | sun protection factor |

| | |
|---|---|
| ssUVR | solar-simulated ultraviolet radiation |
| TGF-β | transforming growth factor β |
| UV | ultraviolet |
| UVA | ultraviolet A |
| UVB | ultraviolet B |
| UVC | ultraviolet C |
| UVR | ultraviolet radiation |
| VEGF | vascular endothelial growth factor |

III. Terms and Methods

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

A-Max:

As used herein, "A-max" is defined as the maximum dose of UVR (such as ssUVR) at which the biological effects of the UVA component of UVR is blocked by a sun protection product (for example, sunscreen). The term "A-max" can also refer to the maximum dose of UVA at which the biological effects of UVA are blocked by a sun protection product. A-max can be measured by identifying the maximum dose that generates insignificant Gene Set Analysis (GSA) results (FDR>0%) with the UVA custom gene sets disclosed herein. Thus, in the context of the present disclosure, "blocking" the biological effects of UVA refers to preventing some or all of the alterations in gene expression that are characteristic of exposure to UVA (the UVA signature) as disclosed herein. In some cases, blocking the effects of UVA refers to insignificant results of GSA (FDR>0%), or the absence of the UVA signature. Blocking the effects of UVA does not require a complete blockade of all biological effects resulting from exposure to UVA. The source of UVR and/or UVA can be from any suitable source, including, for example, a solar simulator or a UVA lamp. A solar simulator is generally used to calculate the SPF of a sun protection product and can also be used to calculate A-max by using in conjunction with a UVB filter.

Array:

An arrangement of molecules, such as biological macromolecules (such as peptides or nucleic acid molecules) or biological samples (such as tissue sections), in addressable locations on or in a substrate. A "microarray" is an array that is miniaturized so as to require or be aided by microscopic examination for evaluation or analysis. Arrays are sometimes called DNA chips or biochips.

The array of molecules ("features") makes it possible to carry out a very large number of analyses on a sample at one time. In certain example arrays, one or more molecules (such as an oligonucleotide probe) will occur on the array a plurality of times (such as twice), for instance to provide internal controls. The number of addressable locations on the array can vary, for example from at least four, to at least 9, at least 10, at least 14, at least 15, at least 20, at least 30, at least 50, at least 75, at least 100, at least 150, at least 200, at least 300, at least 500, least 550, at least 600, at least 800, at least 1000, at least 10,000, or more.

In particular examples, an array includes nucleic acid molecules, such as oligonucleotide sequences that are at least 15 nucleotides in length, such as about 15-40 nucleotides in length.

Within an array, each arrayed sample is addressable, in that its location can be reliably and consistently determined within at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays usually are computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Biopsy:

Refers to the removal of a sample of tissue from a living subject. A "shave biopsy" takes a thin slice of the outermost layers of skin. A "punch biopsy" removes a small disk of tissue using a sharp, hollow instrument. A modified shave/punch biopsy removes a thin slice of skin generally with approximately 1 mm in thickness and about 4 mm in diameter. In some embodiments, the biopsy removes the epidermis and at least part of the dermis. In the context of the present disclosure, the thickness and diameter of the biopsy can vary so long as the skin obtained is suitable for isolation of RNA.

Complementarity and Percentage Complementarity:

Molecules with complementary nucleic acids form a stable duplex or triplex when the strands bind, (hybridize), to each other by forming Watson-Crick, Hoogsteen or reverse Hoogsteen base pairs. Stable binding occurs when an oligonucleotide molecule remains detectably bound to a target nucleic acid sequence under the required conditions.

Complementarity is the degree to which bases in one nucleic acid strand base pair with the bases in a second nucleic acid strand. Complementarity is conveniently described by percentage, that is, the proportion of nucleotides that form base pairs between two strands or within a specific region or domain of two strands. For example, if 10 nucleotides of a 15-nucleotide oligonucleotide form base pairs with a targeted region of a DNA molecule, that oligonucleotide is said to have 66.67% complementarity to the region of DNA targeted.

"Sufficient complementarity" means that a sufficient number of base pairs exist between an oligonucleotide molecule and a target nucleic acid sequence to achieve detectable binding. When expressed or measured by percentage of base pairs formed, the percentage complementarity that fulfills this goal can range from as little as about 50% complementarity to full (100%) complementarity. In general, sufficient complementarity is at least about 50%, for example at least about 75% complementarity, at least about 90% complementarity, at least about 95% complementarity, at least about 98% complementarity, or even at least about 100% complementarity.

A thorough treatment of the qualitative and quantitative considerations involved in establishing binding conditions that allow one skilled in the art to design appropriate oligonucleotides for use under the desired conditions is provided by Beltz et al. (*Methods Enzymol.* 100:266-85, 1983) and by Sambrook et al. (ed.) (*Molecular Cloning: A Laboratory Manual,* 2nd ed., vol. 1-3, Cold Spring Harbor Laboratory Press, Cold Spring Harbor, N.Y., 1989).

Control:

A "control" refers to a sample or standard used for comparison with an experimental sample, such as a skin sample obtained from a test subject exposed to UVR or UVA. In some embodiments, the control is a sample obtained from a subject that has not been exposed to UVR (or specifically UVA) or a non-UVR/UVA exposed sample obtained from the test subject. In some embodiments, the control is a historical control or standard reference value or range of values (i.e. a previously tested control sample, such as a group of skin samples that were not exposed to UVR or UVA, or group of samples that represent baseline or normal values, such as the level of gene expression in non-UVR/UVA exposed tissue).

Differential Expression or Altered Expression:

A difference, such as an increase or decrease, in the conversion of the information encoded in a gene (such as a gene modulated by exposure to UVA) into messenger RNA, the conversion of mRNA to a protein, or both. In some examples, the difference is relative to a control or reference value (or range of values), such as the average expression value of a gene from a group of samples, such as a group of skin samples exposed to UVA. The difference can also be relative to non-UVA exposed tissue from the same subject or a control subject. Detecting differential expression can include measuring a change in gene or protein expression, such as a change in expression of one or more UVA exposure-associated genes.

Downregulated or Decreased:

When used in reference to the expression of a nucleic acid molecule (such as a gene associated with exposure to UVA), refers to any process which results in a decrease in production of a gene product. A gene product can be RNA (such as microRNA, mRNA, rRNA, tRNA, and structural RNA) or protein. Therefore, gene downregulation or deactivation includes processes that decrease transcription of a gene or translation of mRNA.

Examples of processes that decrease transcription include those that facilitate degradation of a transcription initiation complex, those that decrease transcription initiation rate, those that decrease transcription elongation rate, those that decrease processivity of transcription and those that increase transcriptional repression. Gene downregulation can include reduction of expression above an existing level.

Examples of processes that decrease translation include those that decrease translational initiation, those that decrease translational elongation and those that decrease mRNA stability.

Gene downregulation includes any detectable decrease in the production of a gene product. In certain examples, production of a gene product decreases by at least 2-fold, for example at least 3-fold or at least 4-fold, as compared to a control (such as an amount of gene expression in a non-UVA exposed skin sample or in comparison to a reference value).

Efficacy:

Refers to the ability of a compound to produce a particular effect. For example, the efficacy of a drug is a measure of the drug's ability to treat a particular disease or symptom of disease. In the context of the present disclosure, "efficacy" of a sunscreen or other sun protection product refers to the ability of the product to block the effects of UVR or UVA on the skin. Such effects can include sunburn and/or an alteration in gene expression in cells of the skin exposed to UVR and/or UVA.

Epithelial Cells:

Cells that line the exterior of a organism (e.g., skin, cornea), body lumens (e.g., gastrointestinal tract, urinary tract, reproductive tract, lungs) and mucous membranes (e.g., oesophagus, mouth and rectum). Epithelial cells also make up exocrine and endocrine glands.

Erythema:

A redness of the skin caused by dilation of the blood capilaries, such as from inflammation or sunburn.

Expose:

To bring into contact with. As used herein, exposing skin to UVR or UVA generally refers to bringing the skin of a subject in proximity with a source of UVR and/or UVA such that UVR and/or UVA makes contact with the skin.

False Discovery Rate (FDR):

FDR is a measure of the significance in the consistency of up- or down-regulation of gene expression of a defined gene set in a given sample.

Fitzpatrick Skin Typing:

A numerical classification system for the color of skin. It was developed in 1975 by T. B. Fitzpatrick, a Harvard dermatologist, as a way to classify the response of different types of skin to UV light. The Fitzpatrick scale measures several components, including genetic disposition, reaction to sun exposure and tanning habits. The Fitzpatrick Scale defines six types of skin as follows.

Type I (scores 0-7): White, very fair skin; red or blond hair; blue eyes; freckles, always burns and never tans.

Type II (scores 8-16): White, fair skin; red or blond hair; blue, hazel or green eyes; usually burns and tans with difficulty.

Type III (scores 17-25): Creamy white skin; fair with any eye or hair color; sometimes burns mildly and gradually tans.

Type IV (scores 25-30): Dark brown, typical Mediterranean Caucasian skin; rarely burns and tans with ease.

Type V (scores over 30): Dark brown, Middle Eastern skin types; very rarely burns and tans very easily.

Type VI (scores over 30): Black skin; never burns and tans very easily.

Gene Set:

As used herein, a "gene set" is a group of genes that are known to (or have been discovered to) be modulated in response to a particular stimulus, such as UVA exposure. In some cases, a gene set is or comprises a collection of genes involved in a particular signaling or metabolic pathway.

Gene Set Analysis (GSA):

A method for the analysis of changes in gene expression in a particular sample. GSA is a powerful method for identifying signaling pathways that are activated or inactivated in microarray data (such as from human tissues). GSA uses predefined sets of genes that are known to be up- or down-regulated by activation of particular signaling pathways and assesses whether the genes in each gene set are consistently up- or down-regulated in the microarray data of interest. For each gene set, the extent of consistency in up- or down-regulation is presented with a positive and negative score, respectively, and the significance is shown with FDR. If the majority of genes in a gene set that is associated with a particular signaling pathway are consistently modulated, it will result in a significant GSA score to indicate a signature for signaling pathway activation. GSA and other similar methods (such as gene set enrichment analysis—GSEA) have been described (see, for example, Efron and Tibshirani, "On testing the significance of sets of genes," Nov. 3, 2006, available on the World Wide Web at stat.stanford.edu/~tibs/ftp/GSA.pdf; and Subramanian et al., *Proc. Natl. Acad. Sci. USA* 102(43):15545-15550, 2002).

Isolated:

An "isolated" biological component (such as a nucleic acid molecule, protein, or cell) has been substantially separated or purified away from other biological components in the cell of the organism, or the organism itself, in which the component naturally occurs, such as other chromosomal and extra-chromosomal DNA and RNA, proteins and cells. Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules and proteins.

Joule:

A unit of electrical energy equal to the work done when a current of one ampere passes through a resistance of one ohm for one second.

Minimal Erythema Dose (MED):

The lowest amount of UVR required to produce erythema in a subject. Generally, MED is the minimum amount of UVR that causes any redness (even slight redness) of the skin 24 hours after exposure to UVR.

Nucleic Acid Array:

An arrangement of nucleic acids (such as DNA or RNA) in assigned locations on a matrix, such as that found in cDNA arrays, or oligonucleotide arrays.

Purified:

The term "purified" does not require absolute purity; rather, it is intended as a relative term. Thus, for example, a purified nucleic acid preparation is one in which the nucleic acid referred to is more pure than the nucleic acid in its natural environment within a cell. In some examples, a preparation of a nucleic acid is purified such that the nucleic acid represents at least 70%, at least 80%, at least 90%, at least 95 or at least 99% of the total content of the preparation.

Sample (or Biological Sample):

A biological specimen containing genomic DNA, RNA (including mRNA), protein, or combinations thereof, obtained from a subject. Examples include, but are not limited to, peripheral blood, urine, saliva, tissue biopsy, fine needle aspirate, surgical specimen, shave/punch biopsy and autopsy material.

Sequence Identity/Similarity:

The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215: 403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

One indication that two nucleic acid molecules are closely related is that the two molecules hybridize to each other under stringent conditions. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least about 60%, 70%, 80%, 90%, 95%, 98%, or 99% sequence identity to a native nucleic acid sequence of interest, and retain the ability to encode a protein with the same biological activity. An alternative (and not necessarily cumulative) indication that two nucleic acid sequences are substantially identical is that the polypeptide which the first nucleic acid encodes is immunologically cross reactive with the polypeptide encoded by the second nucleic acid.

One of skill in the art will appreciate that the particular sequence identity ranges are provided for guidance only; it is possible that strongly significant homologs could be obtained that fall outside the ranges provided.

Skin:

The outer covering of the body. Skin is made up of two main parts, the epidermis (outer layer) and dermis (inner layer). Skin of any animal is contemplated, including human skin.

Solar-Simulated Ultraviolet Radiation (ssUVR):

Ultraviolet radiation produced by a non-natural source. ssUVR includes UVA, UVB, UVC and visible light with a spectrum profile similar to solar irradiation. Solar simulator devices are well known in the art and are commercially available (such as ORIEL™ solar simulators). "ssUVR" is also referred to as "ssR." In some instances, "UVA" is referred to as "ssA," for example if the source of the UVA is ssUVR in which UVB is blocked with a filter.

Subject:

Living multi-cellular vertebrate organisms, a category that includes human and non-human mammals.

Sun Protection Factor (SPF):

A rating for the degree of protection a particular sunscreen provides against UVB rays.

Sun Protection Product:

Any type of product used to protect the body (such as the skin or eyes) from exposure to ultraviolet radiation. Sun protection products include, for example, sunscreen, cosmetics, UV protective clothing (e.g., hats, shirts, pants, swimwear or other types of clothing) and UV protective eyewear (e.g., sunglasses or goggles).

Sunscreen:

A product that can be applied to the skin that contains at least one chemical that provides protection against UV radiation, such as for the prevention of sunburn or other negative effect of UVR. As used herein, "sunscreen" includes any type of formulation that can be applied to the skin, such as, for example, a cream, foam, lotion or spray.

Treating:

As used herein "treating" the skin of a test subject with a sun protection product includes applying sunscreen (of any type of formulation, such as spray, lotion, foam or gel) to the skin, or covering the skin with sun protective clothing or eyewear.

Ultraviolet Radiation (UVR):

Invisible rays that are part of the energy that comes from the sun. UVR is the portion of the spectrum of electromagnetic radiation of wavelengths between 0.39 and 0.18 μm. UVR can burn the skin and cause skin cancer. Ultraviolet radiation is made up of three types of rays: UVA, UVB and UVC. Although UVC is the most dangerous type of UV light in terms of its potential harm to living organisms, it cannot penetrate earth's protective ozone layer. Therefore, it poses no threat to human, animal or plant life on earth. UVA and UVB do penetrate the ozone layer in attenuated form and reach the surface of the planet. Because the amount of UVA absorbed by DNA is much less than that of UVB, it was previously thought that UVB was the sole culprit in causing skin cancer in people with a history of sunburn and repeated overexposure to ultraviolet radiation. However, recent studies have also implicated UVA as a possible cause of skin cancer. UVB is more likely than UVA to cause sunburn, but UVA passes further into the skin.

Upregulated, Activated or Increased:

When used in reference to the expression of a nucleic acid molecule, such as a gene, refers to any process which results in an increase in production of a gene product. A gene product can be RNA (such as mRNA, rRNA, tRNA, and structural RNA) or protein. Therefore, gene upregulation or activation includes processes that increase transcription of a gene or translation of mRNA.

Examples of processes that increase transcription include those that facilitate formation of a transcription initiation complex, those that increase transcription initiation rate, those that increase transcription elongation rate, those that increase processivity of transcription and those that relieve transcriptional repression (for example by blocking the binding of a transcriptional repressor). Gene upregulation can include inhibition of repression as well as stimulation of expression above an existing level. Examples of processes that increase translation include those that increase translational initiation, those that increase translational elongation and those that increase mRNA stability.

Gene upregulation includes any detectable increase in the production of a gene product. In certain examples, production of a gene product increases by at least 2-fold, for example at least 3-fold or at least 4-fold, as compared to a control (such as an amount of gene expression in a non-UVA exposed skin sample or in comparison to a reference value).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All GenBank Accession numbers listed herein are incorporated by reference in their entirety as they appeared in the NCBI database on Mar. 1, 2010. In case of conflict, the present specification, including explanations of terms, will control. In addition, the materials, methods, and examples are illustrative only and not intended to be limiting.

IV. Overview of Several Embodiments

Disclosed herein is the identification of groups of genes that are either up-regulated or down-regulated in response to UVA exposure. The gene sets described herein can be used to accurately and sensitively identify skin samples that have been exposed to UVA and to assess the ability of a sun protection product to block the biological effects of UVA.

Thus, provided herein is a method for detecting exposure of a skin sample to UVA by detecting expression of a plurality of genes associated with UVA exposure in the skin sample. In some embodiments, the plurality of genes includes (i) AKR1C2, NFIL3, MAP2K3 and BRD1 (referred to herein as the UP4A gene set); or (ii) CAV1, GOLPH3L, H3F3B and SP110 (referred to herein as the DOWN4A gene set); or (iii) both (i) and (ii). An increase in expression of AKR1C2, NFIL3, MAP2K3 and BRD1, or a decrease in expression of CAV1, GOLPH3L, H3F3B and SP110, or both, relative to a control indicates that the skin sample has been exposed to UVA. Accurate results can be obtained when fewer than the recited genes can be analyzed. Therefore, in some examples, the plurality of genes includes AKR1C2, NFIL3 and MAP2K3 (referred to herein as the UP4A-1 gene set), or AKR1C2, NFIL3 and BRD1 (referred to herein as the UP4A-2 gene set).

In some embodiments, the plurality of genes includes AKR1C2, NFIL3, MAP2K3 and BRD1, and further includes one or more of the genes selected from the group consisting of ACSBG1, ADFP, ADH5, AKR1C1, ALDH3A1, AOF2, BDH2, C19orf28, C20orf24, CAPN3, CCDC86, CDC34, CLCA4, CLTB, CTSC, DDX19A, DDX5, ELAC2, FGFBP1, FLJ14154, HK2, HMG20B, HOXB7, KLK10, LONRF1, MYC, OCA2, P11, PMVK, PQBP1, PRKCSH, RPA3, RPL10, SLC25A4, SLTM, SPRR1A, STX4, TMEM160, TPD52L2, TRIM22, TSFM, TUBGCP2, TYR, VIPR1 and WNK1. These genes are part of the UVA gene set referred to as UP_by_A, which represents genes that are up-regulated in response to UVA exposure. Accordingly, in embodiments that use the UP_by_A gene set, or a portion thereof, an increase in expression of the plurality of genes relative to a control indicates the skin sample has been exposed to UVA.

In some embodiments, the plurality of genes includes CAV1, GOLPH3L, H3F3B and SP110, and further includes one or more of the genes selected from the group consisting of CCNG2, CD1A, CD207, CLDND1, FAS, FER1L3, HSPA2, IL33, KIAAO515, KIT, KRT31, LAMB4, MCCC2, PPP1R3C, SCUBE2, THBS2, TMEM43, ZNF652 and ZSCAN18. These genes are part of the UVA gene set referred to as DOWN_by_A, which represents genes that are down-regulated in response to UVA exposure. Accordingly, in embodiments that use the DOWN_by_A gene set, or a portion thereof, a decrease in expression of the plurality of genes relative to a control indicates the skin sample has been exposed to UVA.

In some embodiments, the plurality of genes includes some or all of the genes from both UP_by_A and DOWN_by_A. Gene expression analysis of any combination of genes is contemplated. Additionally, expression of other genes, such as genes that are not modulated by UVA exposure, or housekeeping genes, can be evaluated.

The methods described above can further include analyzing the gene expression data by gene set analysis. In particular embodiments, gene set analysis is carried out using a first UVA gene set or a second UVA gene set to calculate a false discovery rate (FDR) for the sample. The first UVA gene set consists of genes that are up-regulated in response to UVA exposure and the second UVA gene set consists of genes that are down-regulated in response to UVA exposure. A FDR of 0% indicates that the skin sample has been exposed to UVA. In some examples, the gene expression data is analyzed by gene set analysis using the first UVA gene set and the second UVA gene set, wherein a FDR of 0% using the first UVA gene set, a FDR of 0% using the second UVA gene set, or both, indicates that the skin sample has been exposed to UVA.

In some embodiments, the first UVA gene set includes the genes AKR1C2, NFIL3, MAP2K3 and BRD1 (the UP4A gene set); AKR1C2, NFIL3 and MAP2K3 (the UP4A-1 gene set); or AKR1C2, NFIL3 and BRD1 (the UP4A-2 gene set). In some examples, the first UVA gene set further includes one or more of the genes selected from the group consisting of ACSBG1, ADFP, ADH5, AKR1C1, ALDH3A1, AOF2, BDH2, C19orf28, C20orf24, CAPN3, CCDC86, CDC34, CLCA4, CLTB, CTSC, DDX19A, DDX5, ELAC2, FGFBP1, FLJ14154, HK2, HMG20B, HOXB7, KLK10, LONRF1, MYC, OCA2, P11, PMVK, PQBP1, PRKCSH, RPA3, RPL10, SLC25A4, SLTM, SPRR1A, STX4, TMEM160, TPD52L2, TRIM22, TSFM, TUBGCP2, TYR, VIPR1 and WNK1. In some examples, the first UVA gene set consists of AKR1C2, NFIL3, MAP2K3, BRD1ACSBG1, ADFP, ADH5, AKR1C1, ALDH3A1, AOF2, BDH2, C19orf28, C20orf24, CAPN3, CCDC86, CDC34, CLCA4, CLTB, CTSC, DDX19A, DDX5, ELAC2, FGFBP1, FLJ14154, HK2, HMG20B, HOXB7, KLK10, LONRF1, MYC, OCA2, P11, PMVK, PQBP1, PRKCSH, RPA3, RPL10, SLC25A4, SLTM, SPRR1A, STX4, TMEM160, TPD52L2, TRIM22, TSFM, TUBGCP2, TYR, VIPR1 and WNK1 (the UP_by_A gene set).

In some embodiments, the second UVA gene set includes the genes CAV1, GOLPH3L, H3F3B and SP110 (the DOWN4A gene set). In some examples, the second UVA gene set further includes one or more of the genes selected from the group consisting of CCNG2, CD1A, CD207, CLDND1, FAS, FER1L3, HSPA2, IL33, KIAA0515, KIT, KRT31, LAMB4, MCCC2, PPP1R3C, SCUBE2, THBS2, TMEM43, ZNF652 and ZSCAN18. In some examples, the second UVA gene set consists of CAV1, GOLPH3L, H3F3B, SP110, CCNG2, CD1A, CD207, CLDND1, FAS, FER1L3, HSPA2, IL33, KIAAO515, KIT, KRT31, LAMB4, MCCC2, PPP1R3C, SCUBE2, THBS2, TMEM43, ZNF652 and ZSCAN18 (the DOWN_by_A gene set).

In some embodiments where both the first UVA gene set and the second UVA gene set are used, gene set analysis is carried out using all of the genes of the UP_by_A and DOWN_by_A gene sets.

In embodiments of the methods, the skin sample is obtained by biopsy, such as by shave/punch biopsy. Any type of biopsy can be performed as long as sufficient RNA can be obtained from the tissue sample to evaluate gene expression.

In some embodiments, detecting expression of a plurality of genes in the skin sample includes isolating total RNA from the skin sample and subjecting the RNA to microarray analysis. Alternatively, gene expression can be evaluated using any other well known technique, such as quantitative RT-PCR.

In some embodiments, the control is a skin sample from the subject that has not been exposed to UVA. Alternatively, the skin sample can be from another subject that has not been exposed to UVA. In other embodiments, the control is a reference value. For example, the reference value can be an established baseline value for gene expression in samples that were not exposed to UVA.

Also provided herein is a method for determining the efficacy of a sun protection product for providing protection against the effects of UVA. In some embodiments, the method includes treating the skin of a test subject with the sun protection product. The term "treating" in reference to treating a test subject with a sun protection product is intended to include applying a sunscreen product (such as a lotion, spray, foam or gel sunscreen) to the skin, and contacting or covering the skin with sun protective clothing or eyewear. The method further includes exposing the treated skin of the test subject to UVA, and detecting expression of a plurality of genes in a treated skin sample obtained from the subject. In some embodiments, the plurality of genes includes (i) AKR1C2, NFIL3, MAP2K3 and BRD1 (the UP4A gene set); or (ii) CAV1, GOLPH3L, H3F3B and SP110 (the DOWN4A gene set); or (iii) both (i) and (ii). An increase in expression of AKR1C2, NFIL3, MAP2K3 and BRD1, or a decrease in expression of CAV1, GOLPH3L, H3F3B and SP110, or both, relative to a control indicates that the sun protection product does not protect against the effects of UVA. Accurate results can be obtained when fewer than the recited genes can be analyzed. Therefore, in some examples, the plurality of genes includes AKR1C2, NFIL3 and MAP2K3 (the UP4A-1 gene set), or AKR1C2, NFIL3 and BRD1 (the UP4A-2 gene set).

In the context of the present disclosure, "protecting against the effects of UVA" does not require complete protection against all biological effects of UVA, but rather refers to at least partial protection against the changes in gene expression that occur following exposure to UVA. In some examples, a product that protects against the biological effects of UVA in a skin sample is a product that prevents alterations in gene expression such that the UVA signature is not present in the sample.

In some embodiments, the plurality of genes includes AKR1C2, NFIL3, MAP2K3 and BRD1, and further includes one or more of the genes selected from the group consisting of ACSBG1, ADFP, ADH5, AKR1C1, ALDH3A1, AOF2, BDH2, C19orf28, C20orf24, CAPN3, CCDC86, CDC34, CLCA4, CLTB, CTSC, DDX19A, DDX5, ELAC2, FGFBP1, FLJ14154, HK2, HMG20B, HOXB7, KLK10, LONRF1, MYC, OCA2, P11, PMVK, PQBP1, PRKCSH, RPA3, RPL10, SLC25A4, SLTM, SPRR1A, STX4, TMEM160, TPD52L2, TRIM22, TSFM, TUBGCP2, TYR, VIPR1 and WNK1. These genes are part of the UP_by_A gene set, which consists of genes that are up-regulated in response to UVA exposure. Accordingly, in embodiments using the UP_by_A gene set, or portions thereof, an increase in expression of the plurality of genes relative to a control indicates that the sun protection product does not protect against the effects of UVA.

In some embodiments, the plurality of genes includes CAV1, GOLPH3L, H3F3B and SP110, and further includes one or more of the genes selected from the group consisting of CCNG2, CD1A, CD207, CLDND1, FAS, FER1L3, HSPA2, IL33, KIAAO515, KIT, KRT31, LAMB4, MCCC2, PPP1R3C, SCUBE2, THBS2, TMEM43, ZNF652 and ZSCAN18. These genes are part of the DOWN_by_A gene set, which consists of genes that are down-regulated in response to UVA exposure.

Accordingly, in embodiments that use the DOWN_by_A gene set, or a portion thereof, a decrease in expression of the plurality of genes relative to a control indicates that the sun protection product does not protect against the effects of UVA.

In some embodiments, the plurality of genes includes some or all of the genes from both UP_by_A and DOWN_by_A. Gene expression analysis of any combination of genes is contemplated. Additionally, expression of other genes, such as genes that are not modulated by UVA exposure, or housekeeping genes, can be evaluated.

In some embodiments, the methods of determining the efficacy of a sun protection product further includes exposing the skin to multiple different doses of UVA and calculating A-max of the sun protection product, thereby determining the efficacy of the sun protection product.

A-max can be calculated by analyzing the gene expression data by gene set analysis. In some embodiments, gene set analysis is performed using two UVA gene sets to calculate the FDR at each UVA dose. The first UVA gene set consists of genes that are up-regulated in response to UVA exposure and the second UVA gene set consists of genes that are down-regulated in response to UVA exposure. The maximum dose at which the FDR is greater than 0% for both UVA gene sets is A-max for the sun protection product.

In some embodiments of these methods, the first UVA gene set includes the genes AKR1C2, NFIL3, MAP2K3 and BRD1 (the UP4A gene set), or includes AKR1C2, NFIL3 and MAP2K3 (the UP4A-1 gene set) or AKR1C2, NFIL3 and BRD1 (the UP4A-2 gene set). In some examples, first UVA gene set further comprises one or more of the genes selected from the group consisting of ACSBG1, ADFP, ADH5, AKR1C1, ALDH3A1, AOF2, BDH2, C19orf28, C20orf24, CAPN3, CCDC86, CDC34, CLCA4, CLTB, CTSC, DDX19A, DDX5, ELAC2, FGFBP1, FLJ14154, HK2, HMG20B, HOXB7, KLK10, LONRF1, MYC, OCA2, P11, PMVK, PQBP1, PRKCSH, RPA3, RPL10, SLC25A4, SLTM, SPRR1A, STX4, TMEM160, TPD52L2, TRIM22, TSFM, TUBGCP2, TYR, VIPR1 and WNK1. In some examples, the first UVA gene set consists of AKR1C2, NFIL3, MAP2K3, BRD1, ACSBG1, ADFP, ADH5, AKR1C1, ALDH3A1, AOF2, BDH2, C19orf28, C20orf24, CAPN3, CCDC86, CDC34, CLCA4, CLTB, CTSC, DDX19A, DDX5, ELAC2, FGFBP1, FLJ14154, HK2, HMG20B, HOXB7, KLK10, LONRF1, MYC, OCA2, P11, PMVK, PQBP1, PRKCSH, RPA3, RPL10, SLC25A4, SLTM, SPRR1A, STX4, TMEM160, TPD52L2, TRIM22, TSFM, TUBGCP2, TYR, VIPR1 and WNK1 (the UP_by_A gene set).

In some embodiments, the second UVA gene set includes the genes CAV1, GOLPH3L, H3F3B and SP110 (the DOWN4A gene set). In some examples, the second UVA gene set further includes one or more of the genes selected from the group consisting of CCNG2, CD1A, CD207, CLDND1, FAS, FER1L3, HSPA2, IL33, KIAAO515, KIT, KRT31, LAMB4, MCCC2, PPP1R3C, SCUBE2, THBS2, TMEM43, ZNF652 and ZSCAN18. In some examples, the second UVA gene set consists of CAV1, GOLPH3L, H3F3B, SP110, CCNG2, CD1A, CD207, CLDND1, FAS, FER1L3, HSPA2, IL33, KIAAO515, KIT, KRT31, LAMB4, MCCC2, PPP1R3C, SCUBE2, THBS2, TMEM43, ZNF652 and ZSCAN18 (the DOWN_by_A gene set).

In some embodiments where both the first UVA gene set and the second UVA gene set are used, gene set analysis is carried out using all of the genes of the UP_by_A and DOWN_by_A gene sets.

In some embodiments, the skin sample is obtained by biopsy, such as shave/punch biopsy. Any type of biopsy can be performed as long as sufficient RNA can be obtained from the tissue sample to evaluate gene expression.

In some embodiments, detecting expression of a plurality of genes in the skin sample includes isolating total RNA from the skin sample and subjecting the RNA to microarray analysis. Alternatively, gene expression can be evaluated using any other well known technique, such as quantitative RT-PCR.

In some embodiments, the control is a skin sample from the subject that has not been exposed to UVA. Alternatively, the skin sample can be from another subject that has not been exposed to UVA. In other embodiments, the control is a reference value. For example, the reference value can be an established baseline value for gene expression in samples that were not exposed to UVA. The control samples can be skin samples that have either been treated with the sun protection product or left untreated, but generally the control is a sample that has not been exposed to UVA. In particular examples, the control is an untreated skin sample from the subject that has been exposed to UVA.

In some embodiments, the sun protection product is sunscreen, a cosmetic, clothing, eyewear or a sun shield. The sunscreen can be of any formulation, such as a spray, foam, lotion or gel. Similarly, the cosmetic can be in any form (e.g., liquid, spray, powder, gel, foam, or lotion). Sun protective clothing includes any type of garment that is designed to protect against UV (such as UVB). Clothing includes, for example, shirts, pants, skirts, wraps, bathing suits, hats, scarves, socks and the like. Eyewear includes, for example, eyeglasses and goggles. Shields include, for example, the window glass of a building or motor vehicle, and a masking plate of industrial equipment.

In some embodiments, the method of determining the efficacy of a sun protection product includes exposing the skin to multiple different doses of UVA. The number of doses can vary, but generally includes at least two, at least three, at least four, at least five or at least six different doses. Generally, the dose of UVA is measured as the dose of ssUVR before applying a filter to remove UVB. Thus, in some embodiments, one or more of the doses of UVA is the UVA component of at least 100, at least 200, at least 300, at least 400, at least 500 or at least 600 $J/m^2$ of total ssUVR.

Further provided is a method for calculating the maximum dose (A-max) of ultraviolet radiation (UVR) at which a sun protection product blocks the effects of the UVA component of the UVR. In some embodiments, the method includes treating the skin of a test subject with the sun protection product; exposing the skin of the test subject to multiple different doses of UVA; obtaining a skin sample for each UVA dose from the subject; and detecting expression of a plurality of genes in the skin samples obtained from the subject. In some embodiments, the plurality of genes includes (i) AKR1C2, NFIL3, MAP2K3 and BRD1 (the UP4A gene set); or (ii) CAV1, GOLPH3L, H3F3B and SP110 (the DOWN4A gene set); or (iii) both (i) and (ii). Alternatively, plurality of genes can include AKR1C2, NFIL3 and MAP2K3 (the UP4A-1 gene set) or AKR1C2, NFIL3 and BRD1 (the UP4A-2 gene set). The method can further include analyzing the gene expression data by gene set analysis. Gene set analysis can be carried out using a first UVA gene set and a second UVA gene set to calculate a FDR at each UVA dose. The first UVA gene set consists of genes that are up-regulated in response to UVA exposure and the second UVA gene set consists of genes that are down-regulated in response to UVA exposure. The maximum dose at which the FDR is greater than 0% for both the first and second UVA gene sets is A-max for the sun protection product.

In some embodiments of the method for calculating A-max, the plurality of genes includes AKR1C2, NFIL3, MAP2K3 and BRD1, and further includes one or more of the genes selected from the group consisting of ACSBG1, ADFP, ADH5, AKR1C1, ALDH3A1, AOF2, BDH2, C19orf28, C20orf24, CAPN3, CCDC86, CDC34, CLCA4, CLTB, CTSC, DDX19A, DDX5, ELAC2, FGFBP1, FLJ14154, HK2, HMG20B, HOXB7, KLK10, LONRF1, MYC, OCA2, P11, PMVK, PQBP1, PRKCSH, RPA3, RPL10, SLC25A4, SLTM, SPRR1A, STX4, TMEM160, TPD52L2, TRIM22, TSFM, TUBGCP2, TYR, VIPR1 and WNK1 (UP_by_A gene set).

In some embodiments, the plurality of genes includes CAV1, GOLPH3L, H3F3B and SP110, and further includes one or more of the genes selected from the group consisting of CCNG2, CD1A, CD207, CLDND1, FAS, FER1L3, HSPA2, IL33, KIAA0515, KIT, KRT31, LAMB4, MCCC2, PPP1R3C, SCUBE2, THBS2, TMEM43, ZNF652 and ZSCAN18 (DOWN_by_A gene set).

In some embodiments, the plurality of genes includes some or all of the genes from both UP_by_A and DOWN_by_A. Gene expression analysis of any combination of genes is contemplated. Additionally, expression of other genes, such as genes that are not modulated by UVA exposure, or housekeeping genes, can be evaluated.

In some embodiments, the first UVA gene set includes the genes AKR1C2, NFIL3, MAP2K3 and BRD1 (the UP4A gene set), or includes AKR1C2, NFIL3 and MAP2K3 (the UP4A-1 gene set) or includes AKR1C2, NFIL3 and BRD1 (the UP4A-2 gene set). In some examples, the first UVA gene set further includes one or more of the genes selected from the group consisting of ACSBG1, ADFP, ADH5, AKR1C1, ALDH3A1, AOF2, BDH2, C19orf28, C20orf24, CAPN3, CCDC86, CDC34, CLCA4, CLTB, CTSC, DDX19A, DDX5, ELAC2, FGFBP1, FLJ14154, HK2, HMG20B, HOXB7, KLK10, LONRF1, MYC, OCA2, P11, PMVK, PQBP1, PRKCSH, RPA3, RPL10, SLC25A4, SLTM, SPRR1A, STX4, TMEM160, TPD52L2, TRIM22, TSFM, TUBGCP2, TYR, VIPR1 and WNK1. In some examples, the first UVA gene set consists of AKR1C2, NFIL3, MAP2K3, BRD1, ACSBG1, ADFP, ADH5, AKR1C1, ALDH3A1, AOF2, BDH2, C19orf28, C20orf24, CAPN3, CCDC86, CDC34, CLCA4, CLTB, CTSC, DDX19A, DDX5, ELAC2, FGFBP1, FLJ14154, HK2, HMG20B, HOXB7, KLK10, LONRF1, MYC, OCA2, P11, PMVK, PQBP1, PRKCSH, RPA3, RPL10, SLC25A4, SLTM, SPRR1A, STX4, TMEM160, TPD52L2, TRIM22, TSFM, TUBGCP2, TYR, VIPR1 and WNK1 (the UP_by_A gene set).

In some embodiments, the second UVA gene set includes the genes CAV1, GOLPH3L, H3F3B and SP110 (the DOWN4A gene set). In some examples, the second UVA gene set further comprises one or more of the genes selected from the group consisting of CCNG2, CD1A, CD207, CLDND1, FAS, FER1L3, HSPA2, IL33, KIAA0515, KIT, KRT31, LAMB4, MCCC2, PPP1R3C, SCUBE2, THBS2, TMEM43, ZNF652 and ZSCAN18. In some examples, the second UVA gene set consists of CAV1, GOLPH3L, H3F3B, SP110, CCNG2, CD1A, CD207, CLDND1, FAS, FER1L3, HSPA2, IL33, KIAAO515, KIT, KRT31, LAMB4, MCCC2, PPP1R3C, SCUBE2, THBS2, TMEM43, ZNF652 and ZSCAN18.

In some embodiments where both the first UVA gene set and the second UVA gene set are used, gene set analysis is carried out using all of the genes of the UP_by_A and DOWN_by_A gene sets.

In some embodiments, the skin sample is obtained by biopsy, such as shave/punch biopsy. Any type of biopsy can be performed as long as sufficient RNA can be obtained from the tissue sample to evaluate gene expression.

In some embodiments, detecting expression of a plurality of genes in the skin sample includes isolating total RNA from the skin sample and subjecting the RNA to microarray analysis. Alternatively, gene expression can be evaluated using any other well known technique, such as quantitative RT-PCR.

In some embodiments, the sun protection product is sunscreen, a cosmetic, clothing, eyewear or a sun shield. The sunscreen can be of any formulation, such as a spray, foam, lotion or gel. Similarly, the cosmetic can be in any form (e.g., liquid, spray, powder, gel, foam, or lotion). Sun protective clothing includes any type of garment that is designed to protect against UV (such as UVB). Clothing includes, for example, shirts, pants, skirts, wraps, bathing suits, hats, scarves, socks and the like. Eyewear includes, for example, eyeglasses and goggles. Shields include, for example, window glass (such as from a building or a motor vehicle) and a masking plate of industrial equipment.

The number of doses of UVA that are used in these methods can vary, but generally includes at least two, at least three, at least four, at least five or at least six different doses. Generally, the dose of UVA is measured as the dose of ssUVR before applying a filter to remove UVB. Thus, in some embodiments, one or more of the doses of UVA is the UVA component of at least 100, at least 200, at least 300, at least 400, at least 500 or at least 600 J/m$^2$ of total ssUVR.

The gene sets and methods disclosed herein can be used to detect a single (acute) exposure of skin to UVA, or can be used to detect repeated (chronic) exposures. Accordingly, the methods disclosed herein are useful for a number of applications, including for the development of new sunscreens to prevent UVA-induced skin damage, as well as for improved cosmetics to prevent skin tanning.

V. UVA Gene Sets and Gene Set Analysis (GSA)

As used herein, "UVA gene set" refers to a group of genes in which the individual genes of the gene set have been identified as either up-regulated or down-regulated in response to UVA exposure. Collectively, the gene sets can be used to identify samples (such as skin samples) that have been exposed to UVA. Such samples are referred to herein as samples that have the "UVA signature" (with regard to expression of the genes in the gene set).

Provided herein are several particular UVA gene sets. One gene set represents genes that are up-regulated in response to UVA exposure and is called "UP_by_A." A second gene set represents genes that are down-regulated in response to UVA exposure and is called "DOWN_by_A." The UP_by_A gene set consists of ACSBG1, ADFP, ADHS, AKR1C1, AKR1C2, ALDH3A1, AOF2, BDH2, BRD1, C19orf28, C20orf24, CAPN3, CCDC86, CDC34, CLCA4, CLTB, CTSC, DDX19A, DDX5, ELAC2, FGFBP1, FLJ14154, HK2, HMG20B, HOXB7, KLK10, LONRF1, MAP2K3, MYC, NFIL3, OCA2, P11, PMVK, PQBP1, PRKCSH, RPA3, RPL10, SLC25A4, SLTM, SPRR1A, STX4, TMEM160, TPD52L2, TRIM22, TSFM, TUBGCP2, TYR, VIPR1, WNK1. The DOWN_by_A gene set consists of CAV1, CCNG2, CD1A, CD207, CLDND1, FAS, FER1L3, GOLPH3L, H3F3B, HSPA2, IL33, KIAA0515, KIT, KRT31, LAMB4, MCCC2, PPP1R3C, SCUBE2, SP110, THBS2, TMEM43, ZNF652 and ZSCAN18. The gene names and representative accession numbers for the mRNA sequences of the genes are provided in Table 7 and Table 8.

Additional UVA gene sets are provided. For example, the "UP_in_SS" and "DOWN_in_SS" gene sets represent genes that are up-regulated or down-regulated, respectively, in sunscreen+1 MED ssUVR skin samples. The gene symbols for the genes of these gene sets are shown in FIG. 12.

Core UVA gene sets are also provided herein, including the "UP4A" and "DOWN4A" gene sets. UP4A and DOWN4A each consist of four genes that were up-regulated or down-regulated, respectively, in response to UVA exposure. These gene sets represent subsets of the original UP_by_A and DOWN_by_A gene sets. UP4A consists of AKR1C2, NFIL3, MAP2K3 and BRD1, while DOWN4A consists of CAV1, GOLPH3L, H3F3B and SP110. Further subsets of the UP4A gene set were identified and termed "UP4A-1" and "UP4A-2." The UP4A-1 gene set consists of AKR1C2, NFIL3 and MAP2K3, while the UP4A-2 gene set consists of AKR1C2, NFIL3 and BRD1.

In expression microarray data analysis, classical single-gene approaches that rely on thresholds for fold change and false discovery rate (FDR) have several disadvantages in detecting biological differences, particularly when analyzing the transcripts of biopsied human tissue specimens, where observed changes in gene expression are often moderate (Subramanian et al., *Proc Natl Acad Sci USA* 102:15545-15550, 2005). Therefore, in the studies disclosed herein, gene set analysis (GSA) was performed. GSA is an extremely powerful method in identifying signaling pathways that are activated or inactivated in microarray data of human tissues (Armstrong et al., *Nat Genet* 30:41-47, 2002; Beer et al., *Nat Med* 8:816-824, 2002; Bhattacharjee et al., *Proc Natl Acad Sci USA* 98:13790-13795, 2001; Mootha et al., *Nat Genet* 34:267-273, 2003).

GSA uses predefined sets of genes that are known to be up-regulated or down-regulated by activation of particular signaling pathways, and assesses whether the genes in each gene set are consistently up-regulated or down-regulated in the microarray data of interest. For each gene set, the extent of consistency in up-regulation or down-regulation is presented with a positive and negative score, respectively, and the significance is shown with FDR. If the majority of genes in a gene set that is associated with a particular signaling pathway are consistently modulated, it will result in a significant GSA score to indicate a signature for signaling pathway activation.

To identify genes that are modulated in response to UVA exposure, and subsequently identify the custom UVA gene sets disclosed herein, microarray analysis was performed on RNA samples obtained from biopsies of unexposed skin, and skin exposed to UVR or UVA. In some cases, sunscreen was applied to the skin prior to UV exposure. Microarray analysis described in the Examples below was performed using the GENECHIP™ Human Genome U133A oligonucleotide array from Affymetrix. However, any suitable microarray system could be employed, a number of which are well known in the art and commercially available. Differentially expressed genes were identified by pair-wise comparison using Significance Analysis of Microarrays (SAM; Stanford University). SAM has been previously described (see, for example, U.S. Pat. No. 7,363,165). This method identifies genes with statistically significant differences in expression or other biological characteristics. SAM assigns a score to each gene of the microarray based on the change in gene expression relative to the standard deviation of repeated measurements. For genes with scores greater than an adjustable threshold, SAM uses permutations of the repeated measurements to estimate the percentage of such genes identified by chance, the FDR.

To associate differentially expressed genes with signaling pathways, Ingenuity Pathway Analysis (Ingenuity, Redwood City, Calif.) was performed. Using this analysis, a number of signaling pathways associated with UVR-induced cellular stress were identified as associated with UVA exposure, including pathways involving p53 signaling pathway, nucleotide excision repair, protein ubiquitination, and mitochondrial dysfunction. Pathways associated with cell cycle checkpoint regulation, cell survival and nuclear receptor signaling were also identified. The results of this analysis are shown in FIGS. 10 and 11.

The microarray data obtained in the studies disclosed herein were then evaluated using GSA with 1,892 curated gene sets that are known to be up-regulated or down-regulated by the activation of various cellular signaling pathways (Molecular Signature Database, Broad Institute, Massachusetts Institute of Technology) in order to identify gene sets that are significantly affected by ssUVR, UVA and ssUVR+ sunscreen. The results of this analysis are shown in FIGS. 2, 5 and 13. Although the single-gene analysis suggested that UVA made a limited contribution to the total effect of UVR, GSA demonstrated that comparable numbers of gene sets were affected by ssUVR and UVA.

As another approach to evaluate the extent that UVA contributes to the effect of ssUVR, four custom gene sets were created for GSA. Two UVA gene sets, UP_by_A and DOWN_by_A, were assembled using genes that were up-regulated or down-regulated, respectively, in skin exposed to 1 MED UVA. These genes are shown in FIG. 12 and Tables 7 and 8. As demonstrated herein, these UVA gene sets can be used in GSA to identify samples obtained from skin exposed to UVA (i.e. samples that have the "UVA signature"). Two additional gene sets, UP_in_SS and DOWN_in_SS, include genes that were up-regulated or down-regulated, respectively, in sunscreen+1 MED ssUVR skin samples. These genes are shown in FIG. 12.

The custom UVA gene sets UP_by_A and DOWN_by_A can be used in gene set analysis to determine the presence of UVA signatures in microarray data of various skin conditions. These UVA custom gene sets successfully detected the UVA signature in skin that was treated with sunscreen+ssUVR at doses of as low as 0.1 MED. Moreover, additional custom gene sets were identified, referred to herein as UVA "core" gene sets. The core UVA gene sets, UP4A and DOWN4A include four genes each. It was determined that these gene sets are able to identify the UVA signature in skin samples with a sensitivity and consistency equivalent to the original UP_by_A and DOWN_by_A gene sets. The UP4A-1 and UP4A-2 gene sets, which differ from UP4A by including one less gene, were also capable of identifying the UVA signature with similar efficiency.

The data disclosed herein demonstrate that the use of the UVA custom gene sets in GSA can provide a sensitive way to detect UVA effects in skin that is exposed to UVA doses that are encountered in daily life. This strategy offers a sensitive and objective measure to quantify UVA effects on human skin, and to evaluate the UVA protection efficacy of sunscreens and other sun protection products of interest. Such measures could enhance the development of more effective sun protection products that can protect the skin from adverse effects of UVA.

VI. Detection and Quantification of Gene Expression

The effect of UVA exposure on gene expression in a given sample (such as a skin biopsy sample) can be detected and quantified using any one of a number of methods well known in the art. Generally, gene expression is evaluated by detecting mRNA expressed from the gene(s) of interest. Thus, the disclosed methods can include evaluating mRNA expressed from one or more genes from one or both of the UP_by_A and DOWN_by_A gene sets (or one or more other gene sets disclosed herein).

In some embodiments, RNA is isolated from a skin sample of a subject (such as a biopsy), such as a skin sample that has been exposed to ultraviolet radiation, or more particularly, UVA. Skin samples can also be taken from skin that has been treated or covered with a sun protection product (such as sunscreen) and either exposed or unexposed to UVR or UVA. In addition, mRNA can be isolated from control skin samples that have neither been exposed to UV (or specifically UVA), nor covered or treated with a sun protection product. mRNA can be isolated and quantified using methods well known to one skilled in the art, including commercially available kits.

General methods for mRNA extraction are well known in the art and are disclosed in standard textbooks of molecular biology, including Ausubel et al., *Current Protocols of Molecular Biology*, John Wiley and Sons (1997). In some examples, total RNA can be extracted from tissue specimens using RNEASY™ (Qiagen, Valencia, Calif.). In some examples, RNA isolation can be performed using a purification kit, buffer set and protease from commercial manufacturers, such as QIAGEN™, according to the manufacturer's instructions. For example, total RNA from cells in culture or a tissue sample (such as those obtained from a subject) can be isolated using QIAGEN™ RNeasy mini-columns. Other commercially available RNA isolation kits include MASTERPURE™ and Complete DNA and RNA Purification Kit (EPICENTRE™ Madison, Wis.). Total RNA from tissue samples can be isolated using RNA STAT-60™ (Tel-Test, Friendswood, Tex.). RNA prepared from skin biopsy or other biological sample can be isolated, for example, by cesium chloride density gradient centrifugation.

Many methods of gene expression profiling are based on hybridization analysis of polynucleotides, methods based on sequencing of polynucleotides, and proteomics-based methods. In the context of the present disclosure, methods of evaluating gene expression generally involve amplification of mRNA and hybridization of specific probes to the mRNA for detection and quantification. Thus, these types of methods are discussed below. However, one of ordinary skill in the art will recognize that other techniques are available and can be used to detect and quantify gene expression in a specific sample.

In some embodiments described herein, total RNA extracted from tissue specimens is linearly amplified using a two-cycle cDNA synthesis kit (Affymetrix, Santa Clara, Calif.) and labeled with biotin using an IVT labeling kit (Affymetrix). Biotin-labeled cRNAs are fragmented and can be hybridized to an oligonucleotide array, such as the GENECHIP™ Human Genome U133A oligonucleotide arrays (Affymetrix), which contains information for 14,500 well-characterized genes. However, the oligonucleotide arrays do not need to include a large number of genes. In some examples, the oligonucleotide arrays contain at least 5, at least 10, at least 15, at least 20, at least 25, at least 30, at least 35, at least 40, at least 45, at least 50, at least 55, at least 60, at least 65, at least 70 or all 72 genes of the UP_by_A and DOWN_by_A UVA gene sets.

In some examples, mRNA expression in a sample is quantified using PCR-based methods, such as reverse transcription polymerase chain reaction (RT-PCR) (Weis et al., *Trends in Genetics* 8:263-264, 1992). In some examples, RT-PCR can be used to compare mRNA levels in different samples, such as between UVA-exposed and unexposed skin, with or without treatment with a sun protection product, to characterize patterns of gene expression.

Generally, the first step in gene expression profiling by RT-PCR is the reverse transcription of the RNA template into cDNA, followed by its exponential amplification in a PCR reaction. The reverse transcription step is typically primed using specific primers, random hexamers, or oligo-dT primers, depending on the circumstances and the goal of expression profiling. For example, extracted RNA can be reverse-transcribed using a GENEAMP™ RNA PCR kit (Perkin Elmer, Calif.), following the manufacturer's instructions. The derived cDNA can then be used as a template in the subsequent PCR reaction.

Although the PCR step can use a variety of thermostable DNA-dependent DNA polymerases, in one example, it employs the Taq DNA polymerase, which has a 5'-3' nuclease activity but lacks a 3'-5' proofreading endonuclease activity. TAQMAN™ PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TAQMAN™ RT-PCR can be performed using commercially available equipment, such as, for example, ABI PRISM 7700™ Sequence Detection System (Perkin-Elmer-Applied Biosystems, Foster City, Calif.), or LIGHTCYCLER™ (Roche Molecular Biochemicals, Mannheim, Germany). In one example, the 5' nuclease procedure is run on a real-time quantitative PCR device such as the ABI PRISM 7700™ Sequence Detection System. The system includes a thermocycler, laser, charge-coupled device (CCD), camera and computer. The system amplifies samples in a 96-well format on a thermocycler. During amplification, laser-induced fluorescent signal is collected in real-time through fiber optic cables for all 96 wells, and detected at the CCD. The system includes software for running the instrument and for analyzing the data.

To minimize errors and the effect of sample-to-sample variation, RT-PCR can be performed using an internal standard. The ideal internal standard is expressed at a constant level among different tissues, and is unaffected by the experimental treatment. RNAs commonly used to normalize patterns of gene expression are mRNAs for the housekeeping genes glyceraldehyde-3-phosphate-dehydrogenase (GAPDH), beta-actin, and 18S ribosomal RNA.

The primers used for PCR amplification are selected so as to amplify a unique segment of the gene of interest, such as mRNA encoded by one or more genes of the UP_by_A or DOWN_by_A gene sets. In some embodiments, expression of other genes is also detected. Primers that can be used to amplify genes from the UP_by_A and DOWN_by_A gene sets (as well as the other gene sets disclosed herein) are commercially available or can be designed and synthesized according to well known methods using publicly available sequences.

In some examples, gene expression is identified or confirmed using the microarray technique. In this method, UVA exposure-associated gene nucleic acid sequences of interest (such as oligonucleotide probes that specifically hybridize with UVA-exposure associated mRNA) are plated, or arrayed, on a microchip substrate. The arrayed sequences are then hybridized with mRNA isolated from cells or tissues of interest (such as skin biopsy samples). Just as in the RT-PCR method, the source of mRNA typically is total RNA isolated from skin samples.

In a specific embodiment of the microarray technique, PCR amplified inserts of cDNA clones are applied to a substrate in a dense array. Probes specific for one or more of the genes from one or both of the UVA gene sets UP_by_A and DOWN_by_A (or one or more of the other UVA gene sets provided herein) are applied to the substrate, and the array can consist essentially of, or consist of these sequences. However, the microarray substrates can also include probes that recognize additional sequences (for example, housekeeping genes). The microarrayed nucleic acids are suitable for hybridization under stringent conditions. Fluorescently labeled cDNA probes can be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantification of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for genes of interest. Such methods have been shown to have the sensitivity required to detect rare transcripts, which are expressed at a few copies per cell, and to reproducibly detect at least approximately two-fold differences in the expression levels (Schena et al., *Proc. Natl. Acad. Sci. USA* 93(2):10614-10619, 1996). Microarray analysis can be performed by commercially available equipment, following manufacturer's protocols, such as are supplied with Affymetrix GENE-CHIP™ technology, or Incyte's microarray technology.

A. Array Substrates

The solid support of the array can be formed from an organic polymer.

Suitable materials for the solid support include, but are not limited to: polypropylene, polyethylene, polybutylene, polyisobutylene, polybutadiene, polyisoprene, polyvinylpyrrolidine, polytetrafluroethylene, polyvinylidene difluroide, polyfluoroethylene-propylene, polyethylenevinyl alcohol, polymethylpentene, polycholorotrifluoroethylene, polysulformes, hydroxylated biaxially oriented polypropylene, aminated biaxially oriented polypropylene, thiolated biaxially oriented polypropylene, etyleneacrylic acid, thylene methacrylic acid, and blends of copolymers thereof (see U.S. Pat. No. 5,985,567).

In general, suitable characteristics of the material that can be used to form the solid support surface include: being amenable to surface activation such that upon activation, the surface of the support is capable of covalently attaching a biomolecule such as an oligonucleotide thereto; amenability to "in situ" synthesis of biomolecules; being chemically inert such that at the areas on the support not occupied by the oligonucleotides or proteins (such as antibodies) are not amenable to non-specific binding, or when non-specific binding occurs, such materials can be readily removed from the surface without removing the oligonucleotides or proteins (such as antibodies).

In one example, the solid support surface is polypropylene. Polypropylene is chemically inert and hydrophobic. Non-specific binding is generally avoidable, and detection sensitivity is improved. Polypropylene has good chemical resistance to a variety of organic acids (such as formic acid), organic agents (such as acetone or ethanol), bases (such as sodium hydroxide), salts (such as sodium chloride), oxidizing agents (such as peracetic acid), and mineral acids (such as hydrochloric acid). Polypropylene also provides a low fluorescence background, which minimizes background interference and increases the sensitivity of the signal of interest.

In another example, a surface activated organic polymer is used as the solid support surface. One example of a surface activated organic polymer is a polypropylene material aminated via radio frequency plasma discharge. Such materials are easily utilized for the attachment of nucleotide molecules. The amine groups on the activated organic polymers are reactive with nucleotide molecules such that the nucleotide molecules can be bound to the polymers. Other reactive groups can also be used, such as carboxylated, hydroxylated, thiolated, or active ester groups.

B. Array Formats

A wide variety of array formats can be employed in accordance with the present disclosure. One example includes a linear array of oligonucleotide bands, generally referred to in the art as a dipstick. Another suitable format includes a two-dimensional pattern of discrete cells (such as 4096 squares in a 64 by 64 array). As is appreciated by those skilled in the art, other array formats including, but not limited to slot (rectangular) and circular arrays are equally suitable for use (see U.S. Pat. No. 5,981,185). In some examples, the array is a multi-well plate. In one example, the array is formed on a polymer medium, which is a thread, membrane or film. An example of an organic polymer medium is a polypropylene sheet having a thickness on the order of about 1 mil. (0.001 inch) to about 20 mil., although the thickness of the film is not critical and can be varied over a fairly broad range. The array can include biaxially oriented polypropylene (BOPP) films, which in addition to their durability, exhibit low background fluorescence.

The array formats of the present disclosure can be included in a variety of different types of formats. A "format" includes any format to which the solid support can be affixed, such as microtiter plates (e.g., multi-well plates), test tubes, inorganic sheets, dipsticks, and the like. For example, when the solid support is a polypropylene thread, one or more polypropylene threads can be affixed to a plastic dipstick-type device; polypropylene membranes can be affixed to glass slides. The particular format is, in and of itself, unimportant. All that is necessary is that the solid support can be affixed thereto without affecting the functional behavior of the solid support or any biopolymer absorbed thereon, and that the format (such as the dipstick or slide) is stable to any materials into which the device is introduced (such as clinical samples and hybridization solutions).

The arrays of the present disclosure can be prepared by a variety of approaches. In one example, oligonucleotide or protein sequences are synthesized separately and then attached to a solid support (see U.S. Pat. No. 6,013,789). In another example, sequences are synthesized directly onto the support to provide the desired array (see U.S. Pat. No. 5,554,501). Suitable methods for covalently coupling oligonucleotides and proteins to a solid support and for directly synthesizing the oligonucleotides or proteins onto the support are known to those working in the field; a summary of suitable methods can be found in Matson et al., *Anal. Biochem.* 217: 306-310, 1994. In one example, the oligonucleotides are synthesized onto the support using conventional chemical techniques for preparing oligonucleotides on solid supports (such as see PCT publications WO 85/01051 and WO 89/10977, or U.S. Pat. No. 5,554,501).

A suitable array can be produced using automated means to synthesize oligonucleotides in the cells of the array by laying down the precursors for the four bases in a predetermined pattern. Briefly, a multiple-channel automated chemical delivery system is employed to create oligonucleotide probe populations in parallel rows (corresponding in number to the number of channels in the delivery system) across the substrate. Following completion of oligonucleotide synthesis in a first direction, the substrate can then be rotated by 90° to permit synthesis to proceed within a second (2°) set of rows that are now perpendicular to the first set. This process creates a multiple-channel array whose intersection generates a plurality of discrete cells.

The oligonucleotides can be bound to the polypropylene support by either the 3' end of the oligonucleotide or by the 5' end of the oligonucleotide. In one example, the oligonucleotides are bound to the solid support by the 3' end. However, one of skill in the art can determine whether the use of the 3' end or the 5' end of the oligonucleotide is suitable for bonding to the solid support. In general, the internal complementarity of an oligonucleotide probe in the region of the 3' end and the 5' end determines binding to the support.

In particular examples, the oligonucleotide probes on the array include one or more labels, that permit detection of oligonucleotide probe:target sequence hybridization complexes.

The following examples are provided to illustrate certain particular features and/or embodiments. These examples should not be construed to limit the disclosure to the particular features or embodiments described.

EXAMPLES

Example 1

Materials and Methods

This Example describes the experimental procedures used for the studies described in Example 2.
Human Volunteers Twenty healthy volunteers with Fitzpatrick type II skin (age range of 20-43 years; 7 males and 19 females; see Table 2) were evaluated in this study. None reported a history of phototoxic or photoallergic responses, or skin cancer. Solar-simulated ultraviolet radiation (ssUVR) including UVC, UVB, UVA and visible light with a spectrum profile similar to solar irradiation was produced by an ORIEL™ solar simulator (300 watt full spectrum model #81160, Oriel, Stratford, Conn.). The UVC portion was removed by use of a filter, and ssUVR was delivered on a 2×2 cm area of buttock skin.

On day 1, each volunteer was exposed to five fixed-doses of ssUVR (100, 150, 200, 250 and 300 J/m$^2$) to determine the minimal erythema dose (MED) assessed on the following day. On day 2, MEDs were determined, and then the contralateral buttock was exposed to 1 MED, 0.1 MED, and a fixed-dose of 100 J/m$^2$ ssUVR. The first 10 volunteers (Group 1) were also exposed to UVA, by removing UVB from the ssUVR using a filter, for the same predetermined times that resulted in 1 MED, 0.1 MED, and a fixed-dose of 100 J/m$^2$ ssUVR. The remaining volunteers (Group 2) were exposed to the three doses of ssUVR with and without prior application of FDA-standardized sunscreen (SPF 15) that contains 7% padimate 0 and 3% oxybenzone. On day 3 (24 hours after ssUVR exposure) six modified shave/punch biopsies of 4 mm in diameter were taken from each exposure site, and an additional seventh biopsy specimen was obtained from adjacent non-exposed skin as a control. The modified shave/punch biopsy approach was used to ensure that the specimens contained exclusively epidermis and dermis. The collected specimens were immediately placed in RNALATER™ (Ambion, Austin, Tex.).
RNA Preparation and Hybridization to Oligonucleotide Arrays Total RNA was extracted from tissue specimens using RNEASY™ (Qiagen, Valencia, Calif.), linearly amplified using a two-cycle cDNA Synthesis kit (Affymetrix, Santa Clara, Calif.), and labeled with biotin using an IVT Labeling Kit (Affymetrix). Biotin-labeled cRNAs were fragmented and hybridized to GENECHIP™ Human Genome U133A oligonucleotide arrays (Affymetrix) containing information for 14,500 well characterized genes following the manufacturer's protocol.
Microarray Data Analysis Affymetrix .CEL files were processed by GC Robust Multi-array Average algorithm (GC-RMA; BioConductor). The quality of 140 GENECHIP™ arrays was assessed using RNA degradation plot (BioConductor) and dChip software (Dana-Farber Cancer Institute). Ninety-eight microarrays of superior quality from 14 volunteers (8 from Group 1; 6 from Group 2) were used in the final analysis. Differentially expressed genes were identified by pair-wise comparison using Significance Analysis of Microarrays (SAM; Stanford University) with the thresholds for FDR of 1% and log-transformed fold-change of >0.5 or <−0.5. Differentially modulated gene sets were identified with thresholds for FDR of 0% and 30%. Signaling pathways that were modulated by 1 MED ssUVR were investigated using genes that were up- or down-regulated at FDR of 1% (1,362 and 836 genes, respectively) using Ingenuity Pathway Analysis (Ingenuity, Redwood City, Calif.). The gene set analysis was performed using GSA software (Stanford University) with the 1,892 curated gene sets in Molecular Signatures Database developed for Gene Set Enrichment Analysis (GSEA; available online from the Broad Institute at broadinstitute.org/gsea/).
Custom Gene Sets for Gene Set Analysis Genes that were up- or down-regulated by the UVA component of 1 MED ssUVR in eight volunteers of Group 1 were identified at FDR of 25%, and named as "UP_by_A" and "DOWN_by_A," respectively. The UP_by_A gene set includes 49 genes, while the DOWN_by_A gene set includes 23 genes. Genes that were up- or down-regulated by sunscreen+1 MED ssUVR in six volunteers of Group 2 were identified at FDR of 10%, and named "UP_in_SS" (a set of 16 genes), and "DOWN_in_SS" (a set of 42 genes), respectively. UP_by_A and DOWN_by_A from Group 1 data were applied to the sunscreen+UVR data of Group 2. UP_in_SS and DOWN_in_SS from Group 2 data were applied to the UVA data of Group 1. These custom gene sets were combined with the 1,892 curated gene sets in the Molecular Signatures Database of the Broad Institute, and used to probe microarray data for signatures of UVA exposure. The combined gene sets were also applied to the microarray data of various pathological skin conditions in Gene Expression Omnibus (National Center for Biotechnology Information) to determine the potential contribution of UVA to the following pathological conditions: psoriasis (GSE6710), atopic dermatitis (GSE5667), squamous cell carcinoma (GSE2503), actinic keratosis (GSE2503), nevus and malignant melanoma (GSE3189), and repeated irradiation with ssR, ssA and UBV (GSE21429).

Example 2

Identification of Genes Up- or Down-Regulated in Response to UVA Exposure

This example describes gene sets that can be used for detecting skin that has been exposed to UVA.

Design of the Study

To analyze global gene expression profiles in skin exposed to ssUVR, the unprotected skin of 20 volunteers with Fitzpatrick skin type II was exposed to 1 MED, 0.1 MED and a fixed dose of 100 J/m$^2$ ssUVR (Table 1), and biopsies were taken 24 hours after the exposure. The first 10 volunteers (Group 1) were also exposed to the UVA component that was present in each ssUVR dose (Table 1). The second 10 volunteers (Group 2) were also treated with a sunscreen (SPF 15) that blocks UVB and a portion of UVA with shorter wave lengths (UVA-II), and exposed to the three doses of ssUVR (Table 1). Since the MEDs of 20 volunteers ranged from 150 to 300 J/m$^2$ (238±50 J/m$^2$; mean±SD; Table 2), the fixed dose of 100 J/m$^2$ represented an intermediate dose situated between 1 MED and 0.1 MED.

TABLE 1

Study Design

| Group No. | Number of Volunteers | Treatment | Dose of UVR |
|---|---|---|---|
| 1 | 10 | ssUVR | 1 MED |
|   |    |        | 0.1 MED |
|   |    |        | 100 J/m$^2$ |
|   |    | UVA    | 1 MED |
|   |    |        | 0.1 MED |
|   |    |        | 100 J/m$^2$ |
|   |    | no-UV control | 0 J/m$^2$ |
| 2 | 10 | ssUVR  | 1 MED |
|   |    |        | 0.1 MED |
|   |    |        | 100 J/m$^2$ |
|   |    | sunscreen + ssUVR | 1 MED |
|   |    |        | 0.1 MED |
|   |    |        | 100 J/m$^2$ |
|   |    | no-UV control | 0 J/m$^2$ |

TABLE 2

Study Participants

| Group | Age | Gender | Numeric Score | Skin Type Score | MED (J/m$^2$) |
|---|---|---|---|---|---|
| Pilot study | 25 | F | 21 | 2C | 200 |
|  | 24 | F | 19 | 2C | 300 |

TABLE 2-continued

Study Participants

| Group | Age | Gender | Numeric Score | Skin Type Score | MED (J/m$^2$) |
|---|---|---|---|---|---|
| group | 24 | M | 21 | 2C | 300 |
|  | 43 | M | 33 | 3A | 250 |
|  | 26 | M | 20 | 2C | 200 |
|  | 24 | F | 20 | 2C | 200 |
| Group 1 | 31 | M | 21 | 2C | 300 |
|  | 22 | F | 21 | 2C | 150 |
|  | 26 | F | 21 | 2C | 300 |
|  | 29 | F | 16 | 2C | 200 |
|  | 22 | F | 11 | 2B | 250 |
|  | 31 | F | 17 | 2C | 250 |
|  | 26 | M | 14 | 2B | 250 |
|  | 26 | F | 12 | 2B | 200 |
|  | 25 | F | 23 | 3A | 200 |
|  | 36 | F | 18 | 2C | 200 |
| Group 2 | 26 | F | 19 | 2C | 150 |
|  | 24 | M | 20 | 2C | 300 |
|  | 23 | F | 20 | 2C | 250 |
|  | 22 | F | 17 | 2C | 150 |
|  | 19 | F | 16 | 2C | 300 |
|  | 26 | F | 17 | 2C | 300 |
|  | 26 | F | 13 | 2C | 250 |
|  | 31 | F | 18 | 2B | 250 |
|  | 22 | F | 15 | 2C | 250 |
|  | 20 | M | 18 | 2C | 250 |

Differentially Expressed Genes by ssUVR, UVA, and Sunscreen+ssUVR

Figure 1B:
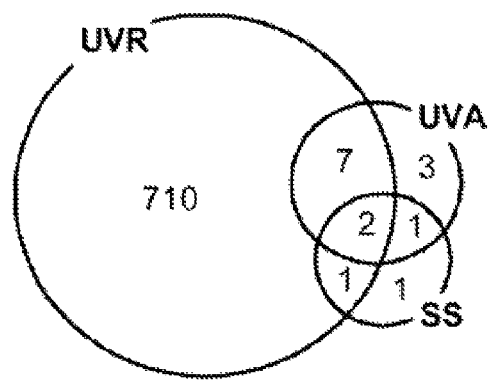
FIG. 1B is a Venn diagram showing the number of genes differentially expressed by 1 MED ssUVR, UVA, and sunscreen+ssUVR (FDR<1%; |log(fold-change)|>0.5). SS in the Venn diagram represents "sunscreen+ssUVR."
Figure 3A:
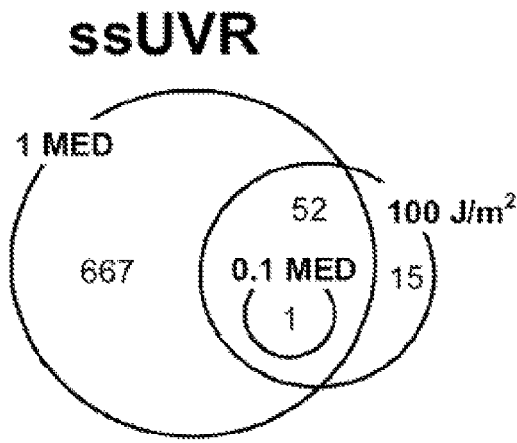
FIGS. 3A and 3B are Venn diagrams showing the number of differentially expressed genes (FDR<1%; |log(fold-change)|>0.5) in the skin treated with 1 MED, 0.1 MED and 100 $J/m^2$ of ssUVR (FIG. 3A) and UVA (FIG. 3B; no hits at 0.1 MED).
Figure 3B:

Genes that were differentially expressed 24 hours after ultraviolet exposure were identified based on the thresholds of |log(fold change)|>0.5 (approximately, >1.4× of up- or down-regulation) and of a FDR of <1% (FIG. 1A). The doses of ssUVR and the numbers of differentially regulated genes showed a dose-response relationship. The number of genes affected by UVA was much lower than by ssUVR, which encompasses both UVB and UVA, and also exhibited a dose-response relationship. Interestingly, sunscreen blocked most of the ssUVR-induced transcriptional changes on single-gene level although substantial changes were revealed later in sunscreen+ssUVR-treated skin using gene set analysis. When individual genes were examined, the majority of genes affected by ssUVR or UVA at 100 J/m$^2$ were also affected at 1 MED (FIG. 3). By comparing genes that were affected by 1 MED ssUVR, UVA, and sunscreen+ssUVR, the contribution of UVA to the ssUVR effect, and the protective efficacy of sunscreen were assessed (FIG. 1B). UVA contributed to only 1% of ssUVR-affected genes (9 of 720). In addition, 4 of 13 UVA-affected genes were not affected by ssUVR, (FIG. 1B). Specifically, three genes (ALDH3A1, CLCA4 and VIPR1; FIG. 7) were up-regulated by UVA, but not by ssUVR even at FDR<5%, suggesting that UVA can induce biological effects that are distinct from those of ssUVR, and possibly can be counteracted by UVB.

By single-gene analysis, sunscreen appeared to block almost all of the ssUVR effects; only 0.4% of the ssUVR-affected genes (3 of 720) were modulated by ssUVR when sunscreen was applied (FIG. 1B). Since this formulation of sunscreen is expected to allow a portion of UVA with longer wave lengths (UVA-I) to pass through, UVA-I may be responsible for the effects on two of the three genes (RPA3 and AKR1C1; FIG. 8). The remaining gene (TYR) was also up-regulated by UVA if the FDR threshold is set to be <5%. Thus, RPA3, AKR1C1 and TYR seem to be affected primarily by UVA-I, which passes through the sunscreen. Additionally, seven genes that were affected either by UVA or ssUVR but not by sunscreen+ssUVR may be affected mostly by UVA-II (FIG. 9).

Signaling Pathways Affected by iMED ssUVR

To associate differentially expressed genes with signaling pathways, Ingenuity Pathway Analysis was performed on 2,198 genes that were found to be differentially expressed by 1 MED ssUVR (FDR<1% without a threshold for fold change; 1,362 up-regulated genes, and 836 down-regulated genes). A number of the signaling pathways were related to ssUVR-induced cellular stress, including p53 signaling, nucleotide excision repair, protein ubiquitination, and mitochondrial dysfunction (FIG. 10 and Table 3). Correspondingly, pathways associated with cell cycle checkpoint regulation were also prominently featured. Additionally, pathways associated with cell survival were affected, including docosahexaenoic acid signaling, insulin receptor and IGF-1 signaling, along with cytokine and chemokine signaling pathways. Of interest, activation of multiple nuclear receptor signaling pathways involving retinoic acid receptor (RAR) and retinoic X receptor (RXR) were prominent, consistent with the important biological effects of retinoic acid on epidermal homeostasis.

TABLE 3

Canonical pathways associated with genes down-regulated by 1 MED ssUVR

| Ingenuity Canonical Pathways | P value | Molecules |
|---|---|---|
| Virus Entry via Endocytic Pathways | 0.000 | FLNB, AP2B1, FYN, ITSN1, PIK3R1, CD55, PIK3C2G, ITGA6, CAV1, ITGB4, CXADR, ITGB5, PRKCB, PRKCA |
| Caveolar-mediated Endocytosis Signaling | 0.000 | FLNB, FYN, FLOT2, ITSN1, CD55, CAV1, ITGA6, FLOT1, ITGB4, ITGB5, PRKCA, EGFR |
| VDR/RXR Activation | 0.000 | CEBPA, NCOA1, IGFBP3, IGFBP5, NCOR2, HES1, CDKN1B, THBD, RXRA, NCOA3, PRKCA, PRKCB |
| Hepatic Fibrosis / Hepatic Stellate Cell Activation | 0.001 | FN1, LEPR, FGFR2, IGFBP5, BCL2, COL1A2, IL1R2, COL1A1, CCL2, IGF1R, CCL21, PDGFRA, IGFBP3, A2M, EGFR, COL3A1 |
| Growth Hormone Signaling | 0.001 | GHR, PIK3R1, IGF1R, CEBPA, IGFBP3, PIK3C2G, JAK2, A2M, PRKCA, PRKCB |
| PPARα/RXRα Activation | 0.002 | ADCY9, ADCY2, GNAQ, JAK2, ABCA1, NCOA3, ACVR1B, IL1R2, GNAS, GHR, CYP2C18, NCOR2, RXRA, ITGB5, PRKCA, PRKCB |
| EGF Signaling | 0.005 | ITPR2, PIK3R1, ITPR3, PIK3C2G, RASA1, PRKCA, EGFR |
| PDGF Signaling | 0.007 | PIK3R1, PDGFRA, CAV1, PIK3C2G, JAK2, RASA1, PDGFC, PRKCA, PRKCB |
| RAR Activation | 0.009 | ADCY9, ADCY2, PRMT2, PIK3R1, JAK2, CRABP1, PNRC1, NCOA1, IGFBP3, NCOR2, RXRA, HLTF, ZBTB16, PRKCA, PRKCB |
| Aldosterone Signaling in Epithelial Cells | 0.010 | ITPR2, PIK3R1, ITPR3, PIK3C2G, SCNN1B, PIP4K2A, NEDD4, PRKCA, PRKCB |
| HER-2 Signaling in Breast Cancer | 0.011 | PIK3R1, PIK3C2G, ITGB4, CDKN1B, PARD3, ITGB5, PRKCA, EGFR, PRKCB |
| CXCR4 Signaling | 0.012 | ADCY9, ADCY2, ITPR2, PIK3R1, PIK3C2G, GNAQ, ROCK2, DOCK1, GNAS, RHOB, ITPR3, GNAL, PRKCB, PRKCA |
| Renin-Angiotensin Signaling | 0.013 | ADCY9, ADCY2, CCL2, ITPR2, PIK3R1, ITPR3, PIK3C2G, GNAQ, JAK2, PRKCA, PRKCB |
| Phospholipase C Signaling | 0.014 | ADCY9, FYN, ADCY2, ITPR2, GNAQ, MEF2A (includes EG:4082), PPP1CB, PLA2G6, GNAS, ARHGEF10, RHOB, AHNAK, ITPR3, MARCKS (includes EG:4082), RALGDS, PPP3CA, PRKCB, PRKCA |
| Thrombin Signaling | 0.014 | ADCY9, ADCY2, ITPR2, PIK3R1, GNAQ, PIK3C2G, ROCK2, GNAS, ARHGEF10, RHOB, ITPR3, GATA3, GNAL, PRKCB, EGFR, PRKCA |
| Cholecystokinin/Gastrin-mediated Signaling | 0.016 | ROCK2, RHOB, ITPR2, ITPR3, MEF2A (includes EG:4205), GNAQ, IL1F7, PRKCA, EGFR, PRKCB |
| Endothelin-1 Signaling | 0.017 | ADCY9, ADCY2, ITPR2, PIK3R1, PTGS1, GNAQ, PIK3C2G, PLA2G6, GNAS, ITPR3, CASP1, GNAL, PRKCB, PRKCA |
| Synaptic Long Term Depression | 0.018 | ADCY9, PLA2G6, GNAS, ADCY2, ITPR2, PPP2R3A, ITPR3, IGF1R, GNAQ, GNAL, PRKCA, PRKCB |
| LPS/IL-1 Mediated Inhibition of RXR Function | 0.019 | GSTM1, APOE, CPT1A, MGMT, ABCA1, IL1R2, GSTM2, UST, GSTM4, FMO1, FABP7, RXRA, ABCC4, ALDH6A1, MGST3 |
| Aryl Hydrocarbon Receptor Signaling | 0.019 | GSTM1, GSTM2, CYP1A2, POLA1, GSTM4, NFIB, NCOR2, CDKN1B, RXRA, ALDH6A1, NCOA3, MGST3 |
| TR/RXR Activation | 0.022 | KLF9, COL6A3, PIK3R1, NCOA1, PIK3C2G, THRA, NCOR2, RXRA, NCOA3 |
| α-Adrenergic Signaling | 0.022 | ADCY9, GNAS, ADCY2, PHKB, ITPR2, ITPR3, GNAQ, PRKCA, PRKCB |
| Xenobiotic Metabolism Signaling | 0.025 | GSTM1, MGMT, PIK3R1, MAF, PIK3C2G, GSTM2, CYP1A2, UST, PPP2R3A, NCOA1, GSTM4, FMO1, NCOR2, RXRA, ALDH6A1, MGST3, PRKCA, PRKCB |
| Mechanisms of Viral Exit from Host Cells | 0.030 | SH3GLB1, SH3GLB2 (includes EG:56904), NEDD4, PRKCA, PRKCB |
| Glucocorticoid Receptor Signaling | 0.032 | HSPA1A, PIK3R1, PBX1, PIK3C2G, JAK2, TAF7, NR3C1, HSPA2, NCOA3, BCL2, IL1R2, TSC22D3, CCL2, NCOA1, CEBPA, NCOR2, HLTF, A2M, PPP3CA |
| G Beta Gamma Signaling | 0.033 | GNAS, ADCY2, CAV1, GNAQ, CAV2, GNAL, PRKCA, EGFR, PRKCB |
| Sphingosine-1-phosphate Signaling | 0.033 | ADCY9, ADCY2, RHOB, PIK3R1, CASP1, PDGFRA, PIK3C2G, GNAQ, PDGFC |
| ILK Signaling | 0.033 | FLNB, FN1, PIK3R1, PIK3C2G, VIM, DOCK1, RHOB, PPP2R3A, PPAP2B, SNAI2, IRS2, RSU1, ITGB4, ITGB5 |
| CCR3 Signaling in Eosinophils | 0.035 | ROCK2, PLA2G6, GNAS, ITPR2, PIK3R1, ITPR3, PIK3C2G, PPP1CB, PRKCA, PRKCB |
| LXR/RXR Activation | 0.039 | IL1R2, APOE, CCL2, NCOR2, IL1F7, RXRA, ABCA1 |
| Non-Small Cell Lung Cancer Signaling | 0.039 | ITPR2, PIK3R1, ITPR3, PIK3C2G, RXRA, PRKCA, EGFR |
| Macropinocytosis Signaling | 0.039 | PIK3R1, PIK3C2G, ITGB4, PDGFC, ITGB5, PRKCA, PRKCB |
| Docosahexaenoic Acid (DHA) Signaling | 0.041 | PIK3R1, SERPINF1, PIK3C2G, APP, BCL2 |
| PXR/RXR Activation | 0.042 | GSTM1, GSTM2, CYP1A2, CPT1A, NCOA1, RXRA, NR3C1 |
| Thrombopoietin Signaling | 0.043 | PIK3R1, PIK3C2G, IRS2, JAK2, PRKCA, PRKCB |
| CDK5 Signaling | 0.043 | ADCY9, GNAS, ADCY2, NTRK2, PPP2R3A, ITGA6, PPP1CB, GNAL |
| Melanocyte Development and Pigmentation Signaling | 0.043 | ADCY9, GNAS, ADCY2, PIK3R1, PIK3C2G, KIT, DCT, BCL2 |
| Glioma Signaling | 0.045 | RBL2, PIK3R1, IGF1R, PDGFRA, PIK3C2G, PDGFC, PRKCA, EGFR, PRKCB |

TABLE 3-continued

Canonical pathways associated with genes down-regulated by 1 MED ssUVR

| Ingenuity Canonical Pathways | P value | Molecules |
|---|---|---|
| Role of Macrophages, Fibroblasts and Endothelial Cells in Rheumatoid Arthritis | 0.047 | FN1, WNT3, PIK3R1, DAAM1, GNAQ, PIK3C2G, IL1F7, JAK2, PDGFC, PAMR1, ROCK2, IL1R2, F2RL1, CCL2, DKK3, CEBPA, WNT4, PPP3CA, PRKCA, PRKCB |
| Prolactin Signaling | 0.051 | FYN, PIK3R1, PIK3C2G, JAK2, NR3C1, PRKCA, PRKCB |
| Human Embryonic Stem Cell Pluripotency | 0.054 | GNAS, NTRK2, WNT3, PIK3R1, PDGFRA, PIK3C2G, BMPR2, WNT4, FGFR2, PDGFC |
| Chemokine Signaling | 0.062 | ROCK2, CCL2, PIK3C2G, GNAQ, PPP1CB, PRKCA, PRKCB |
| Notch Signaling | 0.062 | CNTN1, JAG2, HES1, JAG1 |
| Atherosclerosis Signaling | 0.065 | COL1A2, COL1A1, PLA2G6, CCL2, IL1F7, COL18A1, PDGFC, COL3A1 |
| IGF-1 Signaling | 0.068 | PIK3R1, IGF1R, IGFBP3, PIK3C2G, IGFBP5, IRS2, NEDD4, RASA1 |
| fMLP Signaling in Neutrophils | 0.069 | GNAS, ITPR2, PIK3R1, NCF2, ITPR3, PIK3C2G, PPP3CA, PRKCA, PRKCB |
| Fcγ Receptor-mediated Phagocytosis in Macrophages and Monocytes | 0.072 | DOCK1, FYN, PLA2G6, VAV3, PIK3R1, PIK3C2G, PRKCA, PRKCB |
| Reelin Signaling in Neurons | 0.074 | FYN, APOE, ARHGEF10, PIK3R1, ITGA6, PIK3C2G, APP |
| Molecular Mechanisms of Cancer | 0.078 | ADCY9, FYN, TCF4, ADCY2, PIK3R1, GNAQ, PIK3C2G, BMPR2, JAK2, BCL2, GNAS, CDH1, ARHGEF10, NF1, RHOB, CDKN1B, RASA1, RALGDS, GNAL, PRKCA, CTNND1, PRKCB |
| Corticotropin Releasing Hormone Signaling | 0.079 | ADCY9, GNAS, ADCY2, ITPR2, ITPR3, MEF2A (includes EG:4205), GNAQ, PRKCA, PRKCB |
| Dendritic Cell Maturation | 0.083 | COL1A2, COL1A1, LEPR, CD1A, PIK3R1, PIK3C2G, JAK2, IL1F7, COL18A1, DDR1, COL3A1 |
| NRF2-mediated Oxidative Stress Response | 0.083 | GSTM1, GSTM2, ERP29, PIK3R1, MAF, GSTM4, PIK3C2G, FMO1, MGST3, PRKCA, PRKCB, FTH1 |
| Role of NFAT in Regulation of the Immune Response | 0.085 | FYN, GNAS, ITPR2, PIK3R1, ITPR3, CSNK1D, FCER1A, MEF2A (includes EG:4205), PIK3C2G, GNAQ, PPP3CA, GNAL |
| Fc Epsilon RI Signaling | 0.093 | FYN, PLA2G6, VAV3, PIK3R1, FCER1A, PIK3C2G, PRKCA, PRKCB |
| Coagulation System | 0.098 | PROS1, F13A1, THBD, A2M |
| PPAR Signaling | 0.098 | IL1R2, NCOA1, PDGFRA, NCOR2, IL1F7, RXRA, PDGFC |

Gene Set Analysis on all Genes in the Microarray

In expression microarray data analysis, classical single-gene approaches that rely on thresholds for fold change and FDR have several disadvantages in detecting biological differences, particularly when analyzing the transcripts of biopsied human tissue specimens, where observed changes in gene expression are often moderate (Subramanian et al., *Proc Natl Acad Sci USA* 102:15545-15550, 2005). Therefore, gene set analysis was performed, which is an extremely powerful method in identifying signaling pathways that are activated or inactivated in microarray data of human tissues (Armstrong et al., *Nat Genet* 30:41-47, 2002; Beer et al., Nat Med 8:816-824, 2002; Bhattacharjee et al., *Proc Natl Acad Sci USA* 98:13790-13795, 2001; Mootha et al., *Nat Genet* 34:267-273, 2003). Gene set analysis uses predefined sets of genes that are known to be up- or down-regulated by activation of particular signaling pathways, and assesses whether the genes in each gene set are consistently up- or down-regulated in the microarray data of interest. For each gene set, the extent of consistency in up- or down-regulation is presented with a positive and negative score, respectively, and the significance is shown with FDR. If the majority of genes in a gene set that is associated with a particular signaling pathway are consistently modulated, it will result in a significant GSA score to indicate a signature for signaling pathway activation.

Figure 2A:
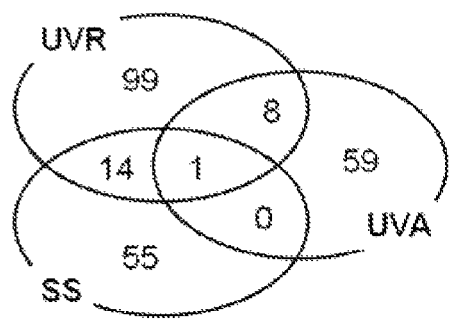
FIGS. 2A and 2B are Venn diagrams showing the number of gene sets affected by 1 MED ssUVR, UVA, and sunscreen+ssUVR (FDR<30% for FIG. 2A; FDR=0% for FIG. 2B).
Figure 2B:
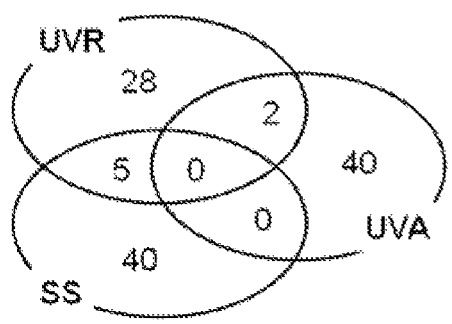

Gene Set Analysis software (GSA; Stanford University) was used with 1,892 curated gene sets that are known to be up- or down-regulated by the activation of various cellular signaling pathways (Molecular Signature Database, Broad Institute) to identify gene sets that are significantly affected by ssUVR, UVA, or sunscreen+ssUVR. Although the single-gene analysis suggested a limited contribution of UVA to the dominant effect of ssUVR (FIG. 1B), GSA demonstrated that comparable numbers of gene sets were affected by ssUVR and UVA (FIGS. 2A and 2B). Additionally, a substantial fraction of ssUVR-affected gene sets were affected also by sunscreen+ssUVR (15 of 122 gene sets at FDR<30% in FIG. 2A; 5 of 35 at FDR=0% in FIG. 2B), arguing that sunscreen may not block important biological effects of ssUVR to the extent suggested by the single-gene analysis (FIG. 1B). The gene sets that were modulated by ssUVR, and not blocked by sunscreen are shown in FIG. 11. These may reflect effects of ssUVR that penetrated the sunscreen. Interestingly, 55 gene sets elicited by sunscreen+ssUVR were not affected by ssUVR alone, suggesting that unique biological effects are elicited in the skin following the treatment with sunscreen and ssUVR (FIG. 2A). GSA also suggested that UVA made greater contributions to the ssUVR effects (9 of 122 gene sets) than suggested by single-gene analysis (FIG. 1B), while 59 gene sets that were elicited by UVA were not affected by ssUVR. The 59 gene sets that were modulated by UVA, and not by ssUVR, include multiple gene sets associated with metabolism of glucose, amino acid and glycerolipid (Table 4).

TABLE 4

Gene sets affected by 1 MED UVA

| | UVA | | UVR | | SS | |
|---|---|---|---|---|---|---|
| Gene_set_name | Score | FDR | Score | FDR | Score | FDR |
| GRANDVAUX_IFN_NOT_IRF3_UP | −1.90 | 0% | −0.05 | 100% | 0.26 | 95% |
| HSA00641_3_CHLOROACRYLIC_ACID_DEGRADATION | 1.56 | 0% | −0.04 | 100% | 0.29 | 65% |
| SARCOMAS_HISTIOCYTOMA_UP | −1.34 | 0% | 0.00 | 100% | −0.40 | 96% |
| LIMONENE_AND_PINENE_DEGRADATION | 1.22 | 0% | 0.00 | 100% | 0.20 | 93% |
| FERRARI_4HPR_UP | −1.09 | 0% | −0.10 | 100% | 0.31 | 78% |
| CALRES_MOUSE_UP | 0.80 | 0% | 0.07 | 84% | 0.13 | 93% |
| PYRUVATE_METABOLISM | 0.78 | 0% | 0.43 | 50% | 0.06 | 93% |
| HSA00650_BUTANOATE_METABOLISM | 0.75 | 0% | 0.21 | 75% | −0.16 | 84% |
| BLEO_HUMAN_LYMPH_HIGH_4HRS_UP | −0.75 | 0% | 0.35 | 29% | 0.28 | 92% |

TABLE 4-continued

Gene sets affected by 1 MED UVA

| Gene_set_name | UVA Score | UVA FDR | UVR Score | UVR FDR | SS Score | SS FDR |
|---|---|---|---|---|---|---|
| LYSINE_DEGRADATION | 0.73 | 0% | 0.19 | 78% | 0.10 | 93% |
| ET743_SARCOMA_6HRS_UP | −0.72 | 0% | 0.06 | 89% | −0.10 | 97% |
| HSA00120_BILE_ACID_BIOSYNTHESIS | 0.69 | 0% | −0.05 | 100% | −0.18 | 83% |
| PHENYLALANINE_METABOLISM | 0.68 | 0% | 0.05 | 89% | −0.23 | 89% |
| HSA00350_TYROSINE_METABOLISM | 0.68 | 0% | 0.16 | 44% | −0.15 | 75% |
| HSA00010_GLYCOLYSIS_AND_GLUCONEOGENESIS | 0.68 | 0% | 0.34 | 34% | −0.03 | 97% |
| HISTIDINE_METABOLISM | 0.67 | 0% | 0.11 | 72% | −0.03 | 97% |
| TYROSINE_METABOLISM | 0.66 | 0% | −0.17 | 93% | 0.07 | 95% |
| HYPOXIA_REG_UP | 0.64 | 0% | −0.30 | 71% | −0.31 | 86% |
| SCHRAETS_MLL_UP | −0.59 | 0% | −0.74 | 67% | −0.40 | 86% |
| BILE_ACID_BIOSYNTHES | 0.57 | 0% | 0.28 | 38% | 0.30 | 57% |
| HALMOS_CEBP_UP | 0.56 | 0% | −0.14 | 88% | 0.00 | 97% |
| HSA00903_LIMONENE_AND_PINENE_DEGRADATION | 0.54 | 0% | −0.52 | 85% | −0.17 | 92% |
| BUTANOATE_METABOLISM | 0.53 | 0% | −0.13 | 99% | 0.27 | 44% |
| HSA00620_PYRUVATE_METABOLISM | 0.53 | 0% | 0.30 | 60% | −0.01 | 97% |
| HSA00220_UREA_CYCLE_AND_METABOLISM_OF_AMINO_GROUPS | 0.52 | 0% | −0.15 | 93% | −0.14 | 83% |
| ELECTRON_TRANSPORTER | 0.52 | 0% | 0.23 | 39% | 0.12 | 69% |
| ADIPOGENESIS_HMSC_CLASS8_DN | −0.51 | 0% | −0.67 | 71% | 0.61 | 85% |
| HSA04940_TYPE_I_DIABETES_MELLITUS | −0.49 | 0% | −0.22 | 85% | −0.25 | 49% |
| HSA00310_LYSINE_DEGRADATION | 0.44 | 0% | 0.10 | 83% | 0.05 | 95% |
| HSA00640_PROPANOATE_METABOLISM | 0.42 | 0% | −0.31 | 92% | −0.08 | 94% |
| PITUITARY_FETAL_UP | −0.41 | 0% | −0.06 | 100% | −0.11 | 94% |
| ASTON_DEPRESSION_DN | −0.39 | 0% | −0.19 | 92% | −0.14 | 83% |
| HSA00410_BETA_ALANINE_METABOLISM | 0.39 | 0% | 0.09 | 79% | 0.11 | 95% |
| GLYCEROLIPID_METABOLISM | 0.39 | 0% | −0.10 | 99% | 0.17 | 93% |
| HSA00561_GLYCEROLIPID_METABOLISM | 0.39 | 0% | −0.03 | 100% | −0.11 | 91% |
| BETA_ALANINE_METABOLISM | 0.34 | 0% | 0.18 | 46% | 0.13 | 93% |
| CHESLER_BRAIN_NEURAL_HIGH_GENES | −0.33 | 0% | −0.10 | 98% | −0.01 | 97% |
| RIBAVIRIN_RSV_DN | −0.30 | 0% | −0.20 | 85% | −0.07 | 92% |
| NOS1PATHWAY | 0.29 | 0% | 0.00 | 100% | −0.08 | 96% |
| IRITANI_ADPROX_VASC | −0.23 | 0% | −0.31 | 62% | −0.04 | 96% |
| HSA04730_LONG_TERM_DEPRESSION | 0.20 | 0% | 0.21 | 24% | −0.14 | 71% |
| COLLER_MYC_UP | 1.37 | 14% | 1.45 | 0% | 0.49 | 86% |
| METHANE_METABOLISM | 0.55 | 14% | 0.00 | 100% | −0.06 | 97% |
| HSA00360_PHENYLALANINE_METABOLISM | 0.49 | 14% | 0.01 | 92% | −0.07 | 96% |
| PROPANOATE_METABOLISM | 0.43 | 14% | −0.24 | 97% | −0.03 | 97% |
| HSA00280_VALINE_LEUCINE_AND_ISOLEUCINE_DEGRADATION | 0.38 | 14% | −0.01 | 100% | 0.11 | 93% |
| ADDYA_K562_HEMIN_TREATMENT | 0.32 | 14% | −0.16 | 85% | 0.05 | 95% |
| LEE_ACOX1_UP | 0.31 | 14% | −0.39 | 67% | −0.17 | 88% |
| GLUCONEOGENESIS | 0.67 | 22% | 0.39 | 28% | −0.03 | 97% |
| GLYCOLYSIS | 0.67 | 22% | 0.39 | 28% | −0.03 | 97% |
| HSA00980_METABOLISM_OF_XENOBIOTICS_BY_CYTOCHROME_P450 | 0.62 | 22% | −0.08 | 100% | −0.04 | 96% |
| HSA00071_FATTY_ACID_METABOLISM | 0.60 | 22% | −0.01 | 100% | 0.08 | 87% |
| HSA00340_HISTIDINE_METABOLISM | 0.58 | 22% | 0.23 | 46% | −0.03 | 97% |
| IDX_TSA_UP_CLUSTER1 | 0.46 | 22% | −0.57 | 82% | −0.24 | 89% |
| HSA04950_MATURITY_ONSET_DIABETES_OF_THE_YOUNG | 0.41 | 22% | 0.41 | 29% | −0.32 | 86% |
| HSA00380_TRYPTOPHAN_METABOLISM | 0.34 | 22% | 0.09 | 71% | −0.07 | 86% |
| TSADAC_PANC50_UP | 0.20 | 22% | 0.18 | 49% | −0.09 | 97% |
| TGFBETA_C4_UP | −1.08 | 24% | 0.00 | 100% | 0.28 | 83% |
| IL7PATHWAY | −1.05 | 24% | −0.56 | 82% | −0.33 | 91% |
| ZMPSTE24_KO_UP | −0.63 | 24% | −0.33 | 80% | −0.45 | 61% |
| NKTPATHWAY | −0.39 | 24% | 0.37 | 29% | 0.22 | 93% |
| HUMAN_CD34_ENRICHED_TRANSCRIPTION_FACTORS | −0.13 | 24% | 0.00 | 92% | −0.03 | 93% |
| BIOSYNTHESIS_OF_STEROIDS | 0.86 | 29% | 1.26 | 14% | 0.25 | 93% |
| WANG_MLL_CBP_VS_GMP_DN | 0.60 | 29% | 0.99 | 0% | 0.54 | 0% |
| CANTHARIDIN_DN | 0.55 | 29% | 1.14 | 0% | 0.51 | 83% |
| HDACI_COLON_SUL24HRS_UP | 0.45 | 29% | 0.70 | 29% | 0.48 | 48% |
| RUTELLA_HEPATGFSNDCS_UP | 0.29 | 29% | −0.10 | 99% | 0.09 | 93% |
| AGED_RHESUS_UP | 0.13 | 29% | 0.12 | 31% | 0.02 | 95% |

Gene sets that were affected by ssUVR (FIG. 2C and FIG. 5) were further evaluated. P53 and nucleotide metabolism gene sets and proteosome gene sets were induced by ssUVR, but not by UVA or sunscreen+ssUVR, implying a major role of UVB in these effects. MYC gene sets were induced by ssUVR, and blocked by sunscreen. However, one of the MYC gene sets (COLLER_MYC_UP) was also induced by UVA. These results suggest a partial contribution of UVA-II to the activation of MYC signaling, which appears to be induced mostly by UVB. One RAS gene set (CROONQUIST_RAS_STROMA_DN) demonstrated significant activation by ssUVR (a negative score for a "DN" gene set means the activation). Importantly, sunscreen did not block this ssUVR effect. Vascular endothelial growth factor (VEGF) inactivation (a negative score for a "UP" gene set) was induced by ssUVR but not by UVA, and was blocked by sunscreen, consistent with a primary role of UVB. The signature of transforming growth factor-β (TGF-β) signal inactivation in sunscreen+ssUVR raises interesting questions. These results suggest that TGF-β signaling that was active in the homeostatic skin before the treatment was inactivated by sunscreen+ssUVR treatment.

Creation of Custom Gene Sets for the UVA Signature

As an alternative approach to evaluate the extent of UVA contribution to the ssUVR effect, four custom gene sets were created (FIG. 12). Two UVA gene sets ("UP_by_A" and "DOWN_by_A") were determined in 1 MED UVA data from Group 1 volunteers as up- and down-regulated genes, respectively. By using the UVA gene sets in GSA on various microarray data, a "UVA signature" could be determined by significant FDR values with positive scores for "UP_by_A," negative scores for "DOWN_by_A" or both. Similarly, two sunscreen+ssUVR gene sets ("UP_in_SS" and "DOWN_in_SS") were determined in sunscreen+1 MED ssUVR data from Group 2 volunteers as up- and down-regulated genes, respectively. When these custom gene sets were used in GSA on publicly available microarray data sets of various skin diseases, there were no significant UVA signatures in any of the skin diseases (FIG. 6 and Table 14) with one exception. The genes in UP_in_SS gene set were significantly down-regulated in melanoma (negative scores indicate the down-regulation of the genes in the gene set). Therefore, these results indicate that the UVA signature or sunscreen+ssUVR signature is not present nonspecifically in perturbed skin. The biological implications in the negative signature of "sunscreen+ssUVR" in melanoma are currently unknown.

Figure 4:
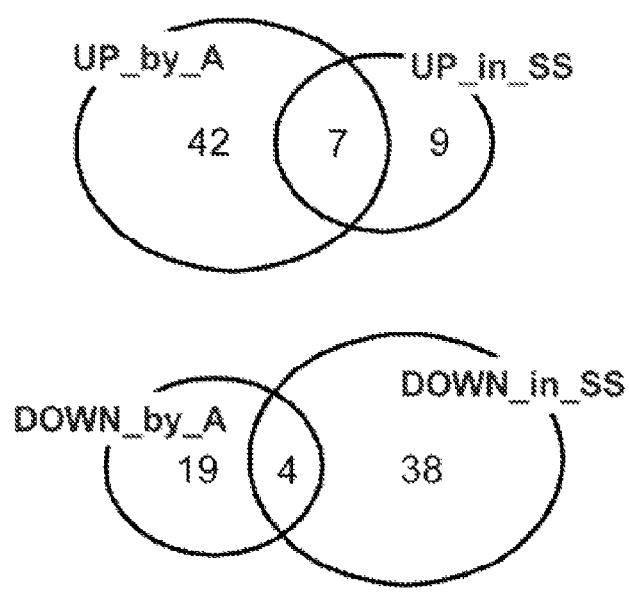
FIG. 4 shows two Venn diagrams illustrating the overlap of genes included in custom gene sets UP_by_A and UP_in_SS, and the overlap of genes included in the DOWN_by_A and DOWN_in_SS gene sets.

The UP_by_A and DOWN_by_A gene sets were used to determine if the UVA signature could be identified in skin that was exposed to ssUVR after treatment with a sunscreen that should block UVB and UVA-II but not UVA-I. When analyzing the sunscreen+ssUVR data, the UP_by_A and DOWN_by_A gene sets detected a UVA signature at all doses of ssUVR: 1 MED, 100 J/m$^2$ and 0.1 MED (FIG. 6). This observation illustrates the sensitivity of this approach to detect the UVA effects in skin. Consistent with the results with UVA gene sets, UP_in_SS and DOWN_in_SS gene sets, when applied to UVA data, detected the positive signature for sunscreen+ssUVR in the skin exposed to 1 MED and 100 J/m$^2$ doses of UVA (FIG. 6). These results are consistent with the overlap between UVA, and sunscreen+ssUVR observed in the single-gene analysis (FIG. 1B, FIG. 7 and FIG. 8). Collectively, these GSA results demonstrate the sensitivity of the custom UVA gene sets in detecting the UVA signature. Additionally, genes that are commonly present in UP_by_A and UP_in_SS, or in DOWN_by_A and DOWN_in_SS (FIG. 4, Table 5 and Table 6) may represent genes affected by UVA-I, which penetrates through the sunscreen.

TABLE 5

UP Genes (common in UP_by_A and UP_in_SS)

| Gene Symbol | Name of Gene Product |
| --- | --- |
| AKR1C1 | Aldo-keto reductase family 1 member C1 |
| AKR1C2 | Aldo-keto reductase family 1 member C2 |
| CLCA4 | Calcium-activated chloride channel regulator 4 |
| LONRF1 | LON peptidase N-terminal domain and RING finger protein 1 |
| MAP2K3 | mitogen-activated protein kinase kinase 3 |
| RPA3 | Replication protein A3 14 kDa subunit |
| TYR | Tyrosinase |

TABLE 6

DOWN genes (common in DOWN_by_A and UP_in_SS)

| Gene Symbol | Name of Gene Product |
| --- | --- |
| CAV1 | Caveolin 1 |
| CCNG2 | Cyclin G2 |

TABLE 6-continued

DOWN genes (common in DOWN_by_A and UP_in_SS)

| Gene Symbol | Name of Gene Product |
| --- | --- |
| GOLPH3L | Golgi phosphoprotein 3-like |
| HSPA2 | Heat shock-related 70 kDa protein 2 |

Summary of Results

Extensive photobiological and epidemiological studies have revealed the pivotal role of ssUVR in skin carcinogenesis. However, little is known about ssUVR effects on the global transcriptome of human skin in vivo, the contribution of UVA to ssUVR effects, and the extent to which sunscreens attenuate ssUVR effects. In non-intentional sun exposure during daily life, the face can be exposed to daily ssUVR dose of 0.1-0.4 MED for indoor workers, and 0.7 MED for outdoor workers (Solar and ultraviolet radiation: World Health Organization, 1997). In order to evaluate the contribution of UVA at this dose range, human skin was exposed to 0.1-1 MED of ssUVR and UVA, and changes in the transcriptome were analyzed. Using the relatively low doses of ultraviolet light on human skin, the studies described herein provide insights that supplement previous global transcriptional analyses of cultured keratinocytes and human skin exposed to higher doses of UVB (Becker et al., *J Invest Dermatol* 116:983-8, 2001; Dazard et al., *Oncogene* 22:2993-3006, 2003; Lee et al., *Br J Dermatol* 152:52-9, 2005; Li et al., *FASEB J* 15-2533-5, 2001; Murakami et al., *J Dermatol Sci* 27:121-9, 2001; Pisarchik et al., *Gene* 341:199-207, 2004; Sesto et al., *Proc Natl Acad Sci USA* 99:2965-70, 2002; Takao et al., *Photodermatol Photoimmunol Photomed* 18:5-13, 2002; Enk et al., *Photodermatol Photoimmunol Photomed* 20:129-37, 2004).

Figure 2C:
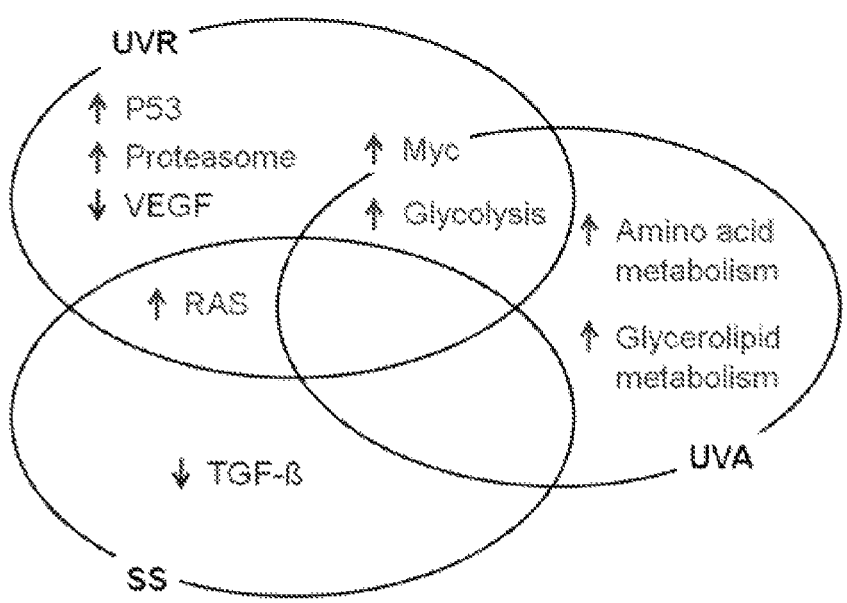
FIG. 2C is a Venn diagram illustrating the signatures for the activation of P53, proteosome, MYC and RAS signaling pathways, and for the inactivation of VEGF signaling pathway by 1 MED ssUVR. Activation of MYC signaling by ssUVR is partially contributed by UVA. Activation of RAS signaling is not blocked by the sunscreen. Inactivation of TGF-β signaling is caused by ssUVR only when the skin is pre-treated with the sunscreen. SS in the Venn diagrams represents "sunscreen+ssUVR."

Gene set analysis demonstrated that comparable numbers of gene sets representing different biological conditions were affected by ssUVR, UVA, and sunscreen+ssUVR (FIGS. 2A and 2B). From the carcinogenesis point of view, it should be noted that the positive signature for MYC signaling was attributed partially to UVA-II, which is blocked by the FDA-standardized sunscreen (FIG. 2C and FIG. 5). Additionally, sunscreen+ssUVR resulted in a negative signature for TGF-β signaling (FIG. 2C and FIG. 5). Given the potential antiproliferative effects of TGF-β on epithelium, this would be an undesirable effect following ssUVR exposure on sunscreen-treated skin. This negative signature could be a vehicle effect, or secondary to the photoreaction between ssUVR and padimate O or oxybenzone. Similarly, 55 gene sets uniquely detected in sunscreen+ssUVR, and not in ssUVR, (FIG. 2A) may be a consequence of the similar mechanisms. The positive signature for RAS signaling that was not blocked by sunscreen (FIG. 5) may have been caused by UVB that was not blocked by the sunscreen. The RAS signaling signature is of concern because activation of RAS signaling is known to play an important role in skin carcinogenesis (Ridky & Khavari, *Cell Cycle* 3:621-4, 2004). It may be important to determine if other sunscreen formulations could better block the ssUVR-induced RAS activation.

Custom gene sets "UP_by_A" and "DOWN_by_A" were created that can be used in gene set analyses to determine the presence of UVA signatures in the microarray data of various skin conditions. These UVA custom gene sets successfully detected the UVA signature in skin that was treated with sunscreen+ssUVR at doses as low as 0.1 MED. Since a sunscreen containing padimate O and oxybenzone was used, neither of which blocks UVA-I, the presence of UVA signature in skin treated with sunscreen+ssUVR was not totally unexpected. The data disclosed herein demonstrate that the use of the UVA custom gene sets in GSA can provide a sensitive way to detect UVA effects in skin that is exposed to UVA doses that are encountered in daily life. This strategy offers a sensitive and objective measure to quantify UVA effects on human skin, and to evaluate the UVA protection efficacy of sunscreens of interest. Such measures could enhance the development of more effective sunscreens that can protect the skin from adverse effects of UVA.

Example 3

Custom Genes Sets for Assessing the Efficacy of Sunscreen Against UVA Exposure

As described in Example 2, two gene sets (UP_by_A and DOWN_by_A) were created that include genes up-regulated or down-regulated when human skin is exposed to the UVA component of 1 minimal erythema dose (MED) of solar-simulated ultraviolet radiation (ssUVR). The UP_by_A gene set consists of 49 human genes, and the DOWN_by_A gene set consists of 23 human genes. The genes in each gene set are shown below in Table 7 and Table 8 by their respective gene symbols. The gene name and a representative GenBank Accession Number for the coding sequence of each gene are also provided. Common alternative gene symbols are provided in parenthesis for some of the genes.

TABLE 7

UVA Gene Set UP_by_A

| Gene Symbol | Gene Name | Accession No. |
| --- | --- | --- |
| ACSBG1 | acyl-CoA synthetase bubblegum family member 1 | NM_015162 |
| ADFP (PLIN2) | Adipocyte differentiation-related protein | NM_001122 |
| ADH5 | alcohol dehydrogenase 5 (class III), chi polypeptide | NM_000671 |
| AKR1C1 | aldo-keto reductase family 1, member C1 | NM_001353 |
| AKR1C2 | aldo-keto reductase family 1, member C2 | NM_001354 |
| ALDH3A1 | aldehyde dehydrogenase 3 family, member A1 | NM_001135168 |
| AOF2 (KDM1A) | amine oxidase (flavin containing) domain 2 | NM_001009999 |
| BDH2 | 3-hydroxybutyrate dehydrogenase, type 2 | NM_020139 |
| BRD1 | bromodomain containing 1 | NM_014577 |
| C19orf28 | chromosome 19 open reading frame 28 | NM_021731 |
| C20orf24 | chromosome 20 open reading frame 24 | NM_018840 |
| CAPN3 | calpain 3, (p94) | NM_000070 |
| CCDC86 | coiled-coil domain containing 86 | NM_024098 |
| CDC34 | cell division cycle 34 homolog | NM_004359 |
| CLCA4 | calcium-activated chloride channel regulator 4 | NM_012128 |
| CLTB | clathrin, light chain (Lcb) | NM_007097 |
| CTSC | cathepsin C | NM_001814 |
| DDX19A | DEAD (Asp-Glu-Ala-As) box polypeptide 19A | NM_018332 |
| DDX5 | DEAD (Asp-Glu-Ala-Asp) box polypeptide 5 | NM_004396 |
| ELAC2 | elaC homolog 2 | NM_018127 |
| FGFBP1 | fibroblast growth factor binding protein 1 | NM_005130 |
| FLJ14154 (NAT15) | N-acetyltransferase 15 (GCN5-related, putative) | NM_001083601 |
| HK2 | hexokinase 2 | NM_000189 |

TABLE 7-continued

UVA Gene Set UP_by_A

| Gene Symbol | Gene Name | Accession No. |
| --- | --- | --- |
| HMG20B | high-mobility group 20B | NM_006339 |
| HOXB7 | homeobox B7 | NM_004502 |
| KLK10 | kallikrein-related peptidase 10 | NM_002776 |
| LONRF1 | LON peptidase N-terminal domain and RING finger 1 | NM_152271 |
| MAP2K3 | mitogen-activated protein kinase kinase 3 | NM_145109 |
| MYC | v-myc myelocytomatosis viral oncogene homolog | NM_002467 |
| NFIL3 | nuclear factor, interleukin 3 regulated | NM_005384 |
| OCA2 | oculocutaneous albinism II | NM_000275 |
| P11 | 26 serine protease | NM_006025 |
| PMVK | phosphomevalonate kinase | NM_006556 |
| PQBP1 | polyglutamine binding protein 1 | NM_005710 |
| PRKCSH | protein kinase C substrate 80K-H | NM_002743 |
| RPA3 | replication protein A3, 14kDa | NM_002947 |
| RPL10 | ribosomal protein L10 | NM_006013 |
| SLC25A4 | solute carrier family 25, member 4 | NM_001151 |
| SLTM | SAFB-like, transcription modulator | NM_024755 |
| SPRR1A | small proline-rich protein 1A | NM_005987 |
| STX4 | syntaxin 4 | NM_004604 |
| TMEM160 | transmembrane protein 160 | NM_017854 |
| TPD52L2 | tumor protein D52-like 2 | NM_199360 |
| TRIM22 | tripartite motif-containing 22 | NM_006074 |
| TSFM | Ts translation elongation factor, mitochondrial | NM_005726 |
| TUBGCP2 | tubulin, gamma complex associated protein 2 | NM_006659 |
| TYR | tyrosinase (oculocutaneous albinism IA) | NM_000372 |
| VIPR1 | vasoactive intestinal peptide receptor 1 | NM_004624 |
| WNK1 | WNK lysine deficient protein kinase 1 | NM_018979 |

TABLE 8

UVA Gene Set DOWN_by_A

| Gene Symbol | Gene Name | Accession No. |
| --- | --- | --- |
| CAV1 | caveolin 1, caveolae protein, 22kDa | NM_001753. |
| CCNG2 | cyclin G2 | NM_004354 |
| CD1A | CD1a molecule | NM_001763 |
| CD207 | CD207 molecule, langerin | NM_015717 |
| CLDND1 | claudin domain containing 1 | NM_001040181 |
| FAS | Fas (TNF receptor superfamily, member 6) | NM_000043 |
| FER1L3 (MYOF) | fer-1-like 3, myoferlin | NM_013451 |
| GOLPH3L | golgi phosphoprotein 3-like | NM_018178 |
| H3F3B | H3 histone, family 3B (H3.3B) | NM_005324 |
| HSPA2 | heat shock 70kDa protein 2 | NM_021979 |
| IL33 | interleukin 33 | NM_033439 |
| KIAA0515 (BAT2L1) | KIAA0515 protein, HLA-B associated transcript 2-like 1 | NM_013318 |
| KIT | v-kit Hardy-Zuckerman 4 feline sarcoma viral oncogene homolog | NM_000222 |
| KRT31 | keratin 31 | NM_002277 |
| LAMB4 | laminin, beta 4 | NM_007356 |
| MCCC2 | methylcrotonoyl-Coenzyme A carboxylase 2 (beta) | NM_022132 |
| PPP1R3C | protein phosphatase 1, regulatory (inhibitor) subunit 3C | NM_005398 |
| SCUBE2 | signal peptide, CUB domain, EGF-like 2 | NM_020974 |
| SP110 | SP110 nuclear body protein | NM_080424 |
| THBS2 | thrombospondin 2 | NM_003247 |
| TMEM43 | transmembrane protein 43 | NM_024334 |
| ZNF652 | zinc finger protein 652 | NM_001145365 |
| ZSCAN18 | zinc finger and SCAN domain containing 18 | NM_001145542 |

These gene sets can be used to determine UVA protection efficacy of sun protection products as A-max by a strategy described below.

Disclosed herein is the development of a method to measure UVA effects on the in vivo transcriptome of human skin using the custom UVA gene sets (UP_by_A and DOWN_by_A) listed above. Custom UVA gene sets are used in gene set analysis with GSA software (Stanford University) to analyze microarray data (such as from Affymetrix HGU133A GENECHIP™). This method forms the basis of the strategy to determine A-max.

In order to determine A-max for a sunscreen of interest, healthy human skin (for example, buttock skin) is exposed to UVA with or without topical sunscreen, biopsied after 24 hours, and analyzed for in vivo transcriptome (changes in gene expression). An example of the experimental design is shown below. In actual studies, doses of UVA can be changed depending on the expected efficacy of the sunscreen of interest.

In this example, twelve 2×2 cm areas on the buttock are used. Six areas are exposed to various doses of UVA without sunscreen pre-treatment. Another six areas are pre-treated with the sunscreen of interest before being exposed to UVA. Individual areas are exposed to increasing doses of UVA. Doses are presented with the ssUVR doses in $J/m^2$, from which the UVB component is removed by a filter to deliver UVA onto the skin. Twenty-four hours after exposure, modified punch/shave biopsies are taken from each area. Total RNA is extracted, labeled, and applied to GENECHIP™. Resultant microarray data are analyzed using the custom UVA gene sets (UP_by_A and DOWN_by_A) disclosed herein and GSA software. When GSA results with custom UVA gene sets are significant (FDR=0%), it means that a "UVA signature" is present in the skin transcriptome, indicating that UVA affected the skin. On the other hand, if GSA results with custom UVA gene sets are insignificant (FDR>0%) in sunscreen-treated skin, it means that a "UVA signature" is absent in the sunscreen-treated skin. Therefore, it is assumed that the sunscreen blocked the UVA effect.

A-max for a sunscreen is defined as the maximum UVA dose that generates insignificant GSA results with both UP_by_A and DOWN_by_A in sunscreen-treated skin. A-max is represented by the dose of ssUVR before removing UVB with a filter. Because ssUVR from a solar simulator provides much better simulation of solar radiation than UVA from a UVA lamp, UVB from a UVB lamp, or a mixture of both, it is generally used for testing sun protection factor (SPF) of sunscreens. Importantly, sunscreen (−) skin has to show significant GSA results (FDR=0%) at corresponding UVA doses as a positive control for UVA signature to ascertain the quality of experiments.

When assessing a sunscreen (Sunscreen A) for its efficacy in blocking UVA, hypothetical GSA results can be such as shown in Table 9 below. In this case, A-max of Sunscreen A is determined as "300" because the maximum dose that resulted in insignificant results for both UP_by_A and DOWN_by_A is 300.

TABLE 9

A-max of Sunscreen A

| Sunscreen A | | Dose of UVA presented with the original ssUVR dose ($J/m^2$) | | | | | |
|---|---|---|---|---|---|---|---|
| | | 100 | 200 | 300 | 400 | 500 | 600 |
| Sunscreen (−) | FDR for UP_by_A | 0% | 0% | 0% | 0% | 0% | 0% |
| | FDR for DOWN_by_A | 0% | 0% | 0% | 0% | 0% | 0% |
| Sunscreen (+) | FDR for UP_by_A | 100% | 80% | 40% | 20% | 0% | 0% |
| | FDR for DOWN_by_A | 70% | 50% | 30% | 0% | 0% | 0% |

If another sunscreen (Sunscreen B) is tested to generate GSA results as shown in Table 10 below, A-max is determined as "500," indicating that Sunscreen B is more potent than Sunscreen A in UVA blocking efficacy.

TABLE 10

A-max of Sunscreen B

| Sunscreen B | | Dose of UVA presented with the original ssUVR dose ($J/m^2$) | | | | | |
|---|---|---|---|---|---|---|---|
| | | 100 | 200 | 300 | 400 | 500 | 600 |
| Sunscreen (−) | FDR for UP_by_A | 0% | 0% | 0% | 0% | 0% | 0% |
| | FDR for DOWN_by_A | 0% | 0% | 0% | 0% | 0% | 0% |
| Sunscreen (+) | FDR for UP_by_A | 100% | 80% | 60% | 40% | 20% | 0% |
| | FDR for DOWN_by_A | 90% | 70% | 50% | 30% | 10% | 0% |

Currently, all sunscreens on the market are required to present sun protection factor (SPF) on their labels. SPF is measured by the fold-increase of time to cause erythema. Since UVB is 1,000 times more erythemogenic than UVA, SPF is primarily a measurement of UVB blockade, and does not measure UVA blocking efficacy. Currently, there are no standard methods to evaluate sunscreens for UVA blocking efficacy. Although labels of many sunscreens state "UVA protection," it is not determined in a standardized way. Therefore, consumers cannot know to what extent those sunscreens block UVA, or whether one sunscreen is better than another in UVA protection.

Since UVA has been increasingly implicated as a cause of melanoma, it is important to develop sunscreens with adequate UVA blocking efficacy, and to provide consumers with information on UVA blocking efficacy of sunscreens of their choice. A-max can appear on the labels of sunscreens along with SPF, (e.g. "SPF 15; A-max 500"). In this way, consumers can choose sunscreens with adequate protection against both UVB and UVA.

The approach disclosed herein offers a sensitive and quantitative measurement of UVA blocking efficacy of sun protection products. As demonstrated by the results provided herein, this method unambiguously detects UVA signatures in sunscreen-treated skin when it is exposed to 0.1 MED (15-30 J/m$^2$) or 1 MED (150-300 J/m$^2$) of ssUVR. Since daily ssUVR doses that reach the faces of indoor workers or outdoor workers are 0.1-0.4 MED and 0.7 MED, respectively, this method is sensitive enough to assess sun protection products for their efficacy in protecting skin from UVA at a dose range that is applicable to daily life.

Example 4

Core Gene Sets for Detection of the UVA Signature

To identify subsets of genes from the UVA custom gene sets that retain the ability to detect the UVA signature, the microarray data sets described in Example 2 were further evaluated. As a result, two new gene sets were identified, UP4A and DOWN4A, each of which contains four genes. UP4A includes AKR1C2, NFIL3, MAP2K3 and BRD1. DOWN4A contains CAV1, GOLPH3L, H3F3B and SP110. As shown in Table 11 and Table 12 below, these gene sets were found to work as well as the original UVA gene sets with equivalent sensitivity and consistency in detecting the UVA signature.

TABLE 11

Comparison of UP_BY_A and UP4A Gene Sets

|  |  | sunscreen + 1 MED ssUVR | sunscreen + 100 J/m$^2$ ssUVR | sunscreen + 0.1 MED ssUVR |
|---|---|---|---|---|
| UP_by_A | score | 2.7 | 1.9 | 1.0 |
|  | FDR | 0% | 0% | 0% |
| UP4A | score | 4.5 | 3.0 | 2.3 |
|  | FDR | 0% | 0% | 0% |

TABLE 12

Comparison of DOWN_by_A and DOWN4A Gene Sets

|  |  | sunscreen + 1 MED ssUVR | sunscreen + 100 J/m$^2$ ssUVR | sunscreen + 0.1 MED ssUVR |
|---|---|---|---|---|
| DOWN_by_A | score | −2.2 | −1.2 | −1.4 |
|  | FDR | 0% | 0% | 0% |
| DOWN4A | score | −2.6 | −1.9 | −2.2 |
|  | FDR | 0% | 0% | 0% |

In addition, it was determined that the UP4A gene set can be further minimized by removal of either BRD1 or MAP2K3, referred to as UP4A-1 or UP4A-2, respectively. Thus, the UP4A-1 gene set contains AKR1C2, NFIL3 and MAP2K3, while the UP4A-2 gene set contains AKR1C2, NFIL3 and BRD1. The UP4A-1 and UP4A-2 gene sets were effective at all doses of ssUVR tested. However, removal of either AKR1C2 or NFIL3 did not allow for identification of the UVA signature at the 0.1 MED ssUVR dose. These results are shown below in Table 13.

TABLE 13

Detection of UVA Signature Using UP4A-1 and UP4A-2

|  |  | sunscreen + 1 MED ssUVR | sunscreen + 100 J/m$^2$ ssUVR | sunscreen + 0.1 MED ssUVR |
|---|---|---|---|---|
| UP4A-1 | score | 4.6 | 2.7 | 2.7 |
|  | FDR | 0% | 0% | 0% |
| UP4A-2 | score | 5.8 | 4.2 | 3.3 |
|  | FDR | 0% | 0% | 0% |
| UP4A minus AKR1 C2 | score | 3.7 | 2.7 | 1.8 |
|  | FDR | 0% | 0% | 43% |
| UP4A minus NFIL3 | score | 3.8 | 2.3 | 1.4 |
|  | FDR | 0% | 0% | 45% |

Further analysis also revealed that the DOWN4A gene set is nearly as effective without either H3F3B or SP110. Removal of either of these genes resulted in a slightly lower consistency for detection of the UVA signature. These results are shown below in Table 14.

TABLE 14

Effect of Removal of a Single Gene from the DOWN4A Gene Set

|  |  | sunscreen + 1 MED ssUVR | sunscreen + 100 J/m$^2$ ssUVR | sunscreen + 0.1 MED ssUVR |
|---|---|---|---|---|
| DOWN4A minus CAV1 | score | −1.9 | −1.6 | −1.7 |
|  | FDR | 32% | 0% | 45% |
| DOWN4A minus GOLPH3L | score | −1.9 | −1.9 | −1.6 |
|  | FDR | 32% | 0% | 45% |
| DOWN4A minus H3F3B | score | −2.8 | −1.4 | −2.4 |
|  | FDR | 0% | 0% | 0% |
| DOWN4A minus SP110 | score | −3.6 | −2.7 | −3.1 |
|  | FDR | 0% | 0% | 0% |

Importantly, none of the core gene sets, or the original UP_by_A or DOWN_by_A gene sets, show pseudo-positive results with microarray data sets of various skin diseases, suggesting that these gene sets are not detecting non-specific skin condition disturbances.

Example 5

Custom Gene Sets for Evaluation of Human Skin Following Repeated ssUVR or UVA Exposure The custom UVA gene sets were also used to assess UVA signatures in human skin that had been irradiated repeatedly with suberythemogenic doses of ssUVR, UVA or UVB over two weeks (Choi et al., *J Invest Dermatol* 130:1685-1696, 2010; incorporated herein by reference). The UP_by_A gene set detected the UVA signature in the skin irradiated with repeated doses of ssUVR or UVA, but not of UVB, indicating that the UP_by_A signature is common for acute and repeated ssUVR irradiation (Table 15). In contrast, the DOWN_by_A signature was absent in the skin with repeated irradiation. This is consistent with the different responses of certain genes to repeated versus acute ssUVR irradiation.

TABLE 15

Gene set analysis with UVA custom gene sets following repeated exposure

| Skin Conditions | UP_BY_A | | DOWN_by_A | |
|---|---|---|---|---|
| | Score[1] | FDR[2] | Score[1] | FDR[2] |
| Sunscreen + ssUVR, 1 MED | 2.67 | 0% | −2.15 | 0% |
| Sunscreen + ssUVR, 100 J/m² | 1.86 | 0% | −1.22 | 0% |
| Sunscreen + ssUVR, 0.1 MED | 1.04 | | −1.41 | 0% |
| Repetitive ssUVR, 0.4 MED X5 + 0.5 MED X5 in two weeks[3] | 0.77 | 0% | 0.02 | 55% |
| Repetitive UVA, 2.3 times the UVA dose in the repetitive ssUVR irradiation[3] | 0.56 | 0% | 0.00 | 100% |
| Repetitive UVB, 1.1 times the UVB dose in the repetitive ssR irradiation[3] | 0.02 | 0% | 0.24 | 85% |

[1] Score indicates the level of consistency of all genes in each gene set for up- or down-regulation. A positive score indicates consistent up-regulation; a negative score indicates consistent down-regulation.
[2] FDR = false discovery rate
[3] These data were obtained from Gene Expression Omnibus (on the World Wide Web at ncbi.nlm.nih.gov/geo/)

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method for detecting gene expression in a skin sample exposed to ultraviolet A (UVA), comprising:
(i) detecting an increase in expression of a first UVA gene set and a decrease in expression of a second UVA gene set in the skin sample relative to a control, wherein the first UVA gene set comprises AKR1C2, NFIL3, MAP2K3 and BRD1 and the second UVA gene set comprises CAV1, GOLPH3L, H3F3B and SP110; and
(ii) calculating a false discovery rate (FDR) for the skin sample using gene set analysis of the first UVA gene set and the second UVA gene set.

2. The method of claim 1, wherein the first UVA gene set further comprises one or more of the genes selected from the group consisting of ACSBG1, ADFP, ADH5, AKR1C1, ALDH3A1, AOF2, BDH2, C19orf28, C20orf24, CAPN3, CCDC86, CDC34, CLCA4, CLTB, CTSC, DDX19A, DDX5, ELAC2, FGFBP1, FLJ14154, HK2, HMG20B, HOXB7, KLK10, LONRF1, MYC, OCA2, P11, PMVK, PQBP1, PRKCSH, RPA3, RPL10, SLC25A4, SLTM, SPRR1A, STX4, TMEM160, TPD52L2, TRIM22, TSFM, TUBGCP2, TYR, VIPR1 and WNK1.

3. The method of claim 1, wherein the second UVA gene set further comprises one or more of the genes selected from the group consisting of CCNG2, CD1A, CD207, CLDND1, FAS, FER1L3, HSPA2, IL33, KIAA0515, KIT, KRT31, LAMB4, MCCC2, PPP1R3C, SCUBE2, THBS2, TMEM43, ZNF652 and ZSCAN18.

4. The method of claim 1, wherein the skin sample was obtained by biopsy.

5. The method of claim 1, wherein detecting an increase or decrease in expression of the first UVA gene set and the second UVA gene set in the skin sample comprises isolating total RNA from the skin sample and subjecting the RNA to microarray analysis.

6. The method of claim 1, wherein the control is a skin sample from the subject that has not been exposed to UVA.

7. The method of claim 1, wherein the control is a reference value.

8. A method for detecting gene expression in a skin sample treated with a sun protection product and exposed to UVA, comprising:
treating the skin of a test subject with the sun protection product to produce treated skin;
exposing the treated skin of the test subject to UVA;
detecting an increase in expression of a first UVA gene set and a decrease in expression of a second UVA gene set in a skin sample obtained from the treated skin of the subject relative to a control, wherein the first UVA gene set comprises AKR1C2, NFIL3, MAP2K3 and BRD1 and the second UVA gene set comprises CAV1, GOLPH3L, H3F3B and SP110; and
calculating a false discovery rate (FDR) for the skin sample using gene set analysis of the first UVA gene set and the second UVA gene set.

9. The method of claim 8, wherein the first UVA gene set further comprises one or more of the genes selected from the group consisting of ACSBG1, ADFP, ADH5, AKR1C1, ALDH3A1, AOF2, BDH2, C19orf28, C20orf24, CAPN3, CCDC86, CDC34, CLCA4, CLTB, CTSC, DDX19A, DDX5, ELAC2, FGFBP1, FLJ14154, HK2, HMG20B, HOXB7, KLK10, LONRF1, MYC, OCA2, P11, PMVK, PQBP1, PRKCSH, RPA3, RPL10, SLC25A4, SLTM, SPRR1A, STX4, TMEM160, TPD52L2, TRIM22, TSFM, TUBGCP2, TYR, VIPR1 and WNK1.

10. The method of claim 8, wherein the second UVA gene set further comprises one or more of the genes selected from the group consisting of CCNG2, CD1A, CD207, CLDND1, FAS, FER1L3, HSPA2, IL33, KIAA0515, KIT, KRT31, LAMB4, MCCC2, PPP1R3C, SCUBE2, THBS2, TMEM43, ZNF652 and ZSCAN18.

11. The method of claim 8, wherein the skin sample was obtained by biopsy.

12. The method of claim 8, wherein detecting an increase or decrease in expression of the first UVA gene set and the second UVA gene set in the skin sample comprises isolating total RNA from the skin sample and subjecting the RNA to microarray analysis.

13. The method of claim 8, wherein the sun protection product is sunscreen, a cosmetic, clothing, eyewear or a sun shield.

14. The method of claim 8, wherein the control is an untreated skin sample from the subject that has been exposed to UVA.

15. The method of claim 8, wherein the control is a reference value.

16. A method for detecting gene expression in a skin sample treated with a sun protection product and exposed to UVA, comprising:
treating the skin of a test subject with the sun protection product to produce treated skin;
exposing the treated skin of the test subject to multiple different doses of UVA;
obtaining a treated skin sample for each UVA dose from the subject;
calculating the maximum close (A-max) of ultraviolet radiation (UVR) at which the sun protection product blocks the effects of the UVA component of the UVR, wherein calculating A-max comprises (i) detecting an increase in expression of a first UVA gene set and a decrease in expression of a second UVA gene set in the treated skin samples relative to a control, wherein the first UVA gene set comprises AKR1C2, NFIL3, MAP2K3 and BRD1 and the second UVA gene set comprises CAV1, GOLPH3L, H3F3B and SP110; and calculating a FDR at each UVA dose using gene set analysis of the first UVA gene set and the second UVA gene set.

17. The method of claim 16, wherein the first UVA gene set further comprises one or more of the genes selected from the group consisting of ACSBG1, ADFP, ADH5, AKR1C1, ALDH3A1, AOF2, BDH2, C19orf28, C20orf24, CAPN3, CCDC86, CDC34, CLCA4, CLTB, CTSC, DDX19A, DDX5, ELAC2, FGFBP1, FLJ14154, HK2, HMG20B, HOXB7, KLK10, LONRF1, MYC, OCA2, P11, PMVK, PQBP1, PRKCSH, RPA3, RPL10, SLC25A4, SLTM, SPRR1A, STX4, TMEM160, TPD52L2, TRIM22, TSFM, TUBGCP2, TYR, VIPR1 and WNK1.

18. The method of claim 16, wherein the second UVA gene set further comprises one or more of the genes selected from the group consisting of CCNG2, CD1A, CD207, CLDND1, FAS, FER1L3, HSPA2, IL33, KIAA0515, KIT, KRT31, LAMB4, MCCC2, PPP1R3C, SCUBE2, THBS2, TMEM43, ZNF652 and ZSCAN18.

19. The method of claim 16, wherein the skin samples are obtained by biopsy.

20. The method of claim 16, wherein the sun protection product is sunscreen, a cosmetic, clothing or eyewear.

21. The method of claim 16, wherein the skin is exposed to at least 3, at least 4, at least 5, or at least 6 different doses of UVA.

22. The method of claim 16, wherein one or more of the doses of UVA is the UVA component of at least 100, at least 200, at least 300, at least 400, at least 500 or at least 600 $J/m^2$ of total UVR.

23. The method of claim 16, wherein A-max is at least 100 $J/m^2$.

24. The method of claim 16, wherein A-max is at least 200 $J/m^2$.

25. The method of claim 16, wherein A-max is at least 300 $J/m^2$.

26. The method of claim 16, wherein A-max is at least 400 $J/m^2$.

27. The method of claim 16, wherein A-max is at least 500 $J/m^2$.

28. The method of claim 16, wherein A-max is at least 600 $J/m^2$.

* * * * *